United States Patent
Nguyen et al.

(10) Patent No.: US 10,709,462 B2
(45) Date of Patent: Jul. 14, 2020

(54) LOW PROFILE ELECTRODES FOR A SHOCK WAVE CATHETER

(71) Applicant: SHOCKWAVE MEDICAL, INC., Fremont, CA (US)

(72) Inventors: Hoa D. Nguyen, San Jose, CA (US); Khanh Vo, Daly City, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 299 days.

(21) Appl. No.: 15/817,073

(22) Filed: Nov. 17, 2017

(65) Prior Publication Data

US 2019/0150960 A1    May 23, 2019

(51) Int. Cl.
*A61B 17/22* (2006.01)
*A61B 18/14* (2006.01)

(52) U.S. Cl.
CPC .... *A61B 17/22022* (2013.01); *A61B 17/2202* (2013.01); *A61B 18/1492* (2013.01); *A61B 2017/22001* (2013.01); *A61B 2017/22021* (2013.01); *A61B 2017/22025* (2013.01); *A61B 2017/22051* (2013.01);

(Continued)

(58) Field of Classification Search
CPC .... A61B 17/22022; A61B 2017/22021; A61B 2017/22025; A61B 2017/22051; A61B 2017/22062; A61B 2017/22098; A61B 18/1492; A61B 18/16; A61B 2018/162
See application file for complete search history.

(56) References Cited

U.S. PATENT DOCUMENTS

| 3,413,976 A | 12/1968 | Roze |
| 3,785,382 A | 1/1974 | Schmidt-Kloiber et al. |
| 3,902,499 A | 9/1975 | Shene |

(Continued)

FOREIGN PATENT DOCUMENTS

| CN | 1269708 A | 10/2000 |
| CN | 102057422 A | 5/2011 |

(Continued)

OTHER PUBLICATIONS

Advisory Action received for U.S. Appl. No. 12/482,995, dated Jun. 2, 2014, 3 pages.

(Continued)

*Primary Examiner* — Robert A Lynch
(74) *Attorney, Agent, or Firm* — Morrison & Foerster LLP

(57) ABSTRACT

The invention provides a device for generating shock waves. The device may comprise an elongated tube and a conductive sheath circumferentially mounted around the elongated tube. The device may further comprise first and second insulated wires extending along the outer surface of the elongated tube. A portion of the first insulated wire is removed to form a first inner electrode, which is adjacent to a first side edge of the conductive sheath. A portion of the second insulated wire is removed to form a second inner electrode, which is adjacent to a second side edge of the conductive sheath. Responsive to a high voltage being applied across the first inner electrode and the second inner electrode, a first shock wave is created across the first side edge and the first inner electrode, and a second shock wave is created across the second side edge and the second inner electrode.

22 Claims, 14 Drawing Sheets

(52) U.S. Cl.
CPC .............. *A61B 2017/22061* (2013.01); *A61B 2017/22062* (2013.01); *A61B 2017/22098* (2013.01)

(56) References Cited

U.S. PATENT DOCUMENTS

| | | | |
|---|---|---|---|
| 4,027,674 A | 6/1977 | Tessler et al. | |
| 4,662,126 A | 5/1987 | Malcolm | |
| 4,671,254 A | 6/1987 | Fair | |
| 4,685,458 A | 8/1987 | Leckrone | |
| 4,809,682 A | 3/1989 | Forssmann et al. | |
| 4,900,303 A | 2/1990 | Lemelson | |
| 5,009,232 A | 4/1991 | Hassler et al. | |
| 5,057,103 A | 10/1991 | Davis | |
| 5,057,106 A | 10/1991 | Kasevich et al. | |
| 5,078,717 A | 1/1992 | Parins et al. | |
| 5,103,804 A | 4/1992 | Abele et al. | |
| 5,152,767 A | 10/1992 | Sypal et al. | |
| 5,152,768 A | 10/1992 | Bhatta | |
| 5,154,722 A † | 10/1992 | Filip | |
| 5,176,675 A | 1/1993 | Watson et al. | |
| 5,245,988 A | 9/1993 | Einars et al. | |
| 5,246,447 A | 9/1993 | Rosen et al. | |
| 5,281,231 A | 1/1994 | Rosen et al. | |
| 5,321,715 A | 6/1994 | Trost | |
| 5,324,255 A | 6/1994 | Passafaro et al. | |
| 5,336,234 A | 8/1994 | Vigil et al. | |
| 5,362,309 A | 11/1994 | Carter | |
| 5,364,393 A | 11/1994 | Auth et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | de la Torre et al. | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | de la Torre et al. | |
| 5,931,805 A | 8/1999 | Brisken | |
| 6,007,530 A | 12/1999 | Doernhoefer et al. | |
| 6,033,371 A | 3/2000 | Torre et al. | |
| 6,083,232 A | 7/2000 | Cox | |
| 6,186,963 B1 | 2/2001 | Schwarze et al. | |
| 6,210,408 B1 | 4/2001 | Chandrasekaran et al. | |
| 6,217,531 B1 | 4/2001 | Reitmajer | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de la Torre et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,736,784 B1 | 5/2004 | Menne et al. | |
| 6,740,081 B2 | 5/2004 | Hilal | |
| 6,755,821 B1 | 6/2004 | Fry | |
| 6,989,009 B2 | 1/2006 | Lafontaine | |
| 7,241,295 B2 | 7/2007 | Maguire | |
| 7,505,812 B1 | 3/2009 | Eggers et al. | |
| 7,569,032 B2 | 8/2009 | Naimark et al. | |
| 7,873,404 B1 | 1/2011 | Patton | |
| 8,556,813 B2 | 10/2013 | Cioanta et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 9,005,216 B2 | 4/2015 | Hakala et al. | |
| 9,011,463 B2 | 4/2015 | Adams et al. | |
| 9,198,825 B2 † | 12/2015 | Katragadda | |
| 9,333,000 B2 | 5/2016 | Hakala et al. | |
| 9,433,428 B2 † | 9/2016 | Hakala | |
| 9,642,673 B2 | 5/2017 | Adams et al. | |
| 9,993,292 B2 | 6/2018 | Adams et al. | |
| 2001/0044596 A1 | 11/2001 | Jaafar | |
| 2002/0045890 A1 | 4/2002 | Brisken et al. | |
| 2002/0177889 A1 | 11/2002 | Brisken et al. | |
| 2003/0004434 A1 | 1/2003 | Greco et al. | |
| 2003/0176873 A1 | 9/2003 | Chernenko et al. | |
| 2003/0229370 A1 | 12/2003 | Miller | |
| 2004/0006333 A1 | 1/2004 | Arnold et al. | |
| 2004/0010249 A1 | 1/2004 | Truckai et al. | |
| 2004/0044308 A1 | 3/2004 | Naimark et al. | |
| 2004/0097963 A1 | 5/2004 | Seddon | |
| 2004/0097996 A1 | 5/2004 | Rabiner et al. | |
| 2004/0162508 A1 | 8/2004 | Uebelacker | |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0113722 A1 | 5/2005 | Schultheiss | |
| 2005/0113822 A1 | 5/2005 | Fuimaono et al. | |
| 2005/0228372 A1 | 10/2005 | Truckai et al. | |
| 2005/0251131 A1 | 11/2005 | Lesh | |
| 2006/0004286 A1 | 1/2006 | Chang et al. | |
| 2006/0069424 A1 | 3/2006 | Acosta et al. | |
| 2006/0184076 A1 | 8/2006 | Gill et al. | |
| 2006/0190022 A1 | 8/2006 | Beyar et al. | |
| 2007/0016112 A1 | 1/2007 | Schultheiss et al. | |
| 2007/0088380 A1 | 4/2007 | Hirszowicz et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zumeris et al. | |
| 2007/0255270 A1 | 11/2007 | Carney | |
| 2007/0282301 A1 | 12/2007 | Segalescu et al. | |
| 2008/0097251 A1 | 4/2008 | Babaev | |
| 2008/0188913 A1 | 8/2008 | Stone et al. | |
| 2009/0041833 A1 | 2/2009 | Bettinger et al. | |
| 2009/0247945 A1 | 10/2009 | Levit et al. | |
| 2009/0254114 A1 | 10/2009 | Hirszowicz et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0114020 A1 | 5/2010 | Hawkins et al. | |
| 2010/0114065 A1 | 5/2010 | Hawkins et al. | |
| 2010/0121322 A1 | 5/2010 | Swanson | |
| 2010/0305565 A1 | 12/2010 | Truckai et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0208185 A1 | 8/2011 | Diamant et al. | |
| 2011/0257523 A1 | 10/2011 | Hastings et al. | |
| 2011/0295227 A1 | 12/2011 | Hawkins et al. | |
| 2012/0071889 A1 | 3/2012 | Mantell et al. | |
| 2012/0095461 A1 | 4/2012 | Herscher et al. | |
| 2012/0116289 A1 | 5/2012 | Hawkins et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0116714 A1 | 5/2013 | Adams et al. | |
| 2013/0150874 A1 | 6/2013 | Kassab | |
| 2014/0005576 A1 | 1/2014 | Adams et al. | |
| 2014/0039513 A1 | 2/2014 | Hakala et al. | |
| 2014/0046229 A1 | 2/2014 | Hawkins et al. | |
| 2014/0052145 A1 | 2/2014 | Adams et al. | |
| 2014/0052147 A1 | 2/2014 | Hakala et al. | |
| 2014/0074111 A1 | 3/2014 | Hakala et al. | |
| 2014/0074113 A1 | 3/2014 | Hakala et al. | |
| 2014/0214061 A1 | 7/2014 | Adams et al. | |
| 2014/0243847 A1 | 8/2014 | Hakala et al. | |
| 2014/0288570 A1 | 9/2014 | Adams | |
| 2015/0073430 A1 | 3/2015 | Hakala et al. | |
| 2015/0238208 A1 | 8/2015 | Adams et al. | |
| 2015/0320432 A1 | 11/2015 | Adams et al. | |
| 2016/0183957 A1 | 6/2016 | Hakala et al. | |
| 2016/0324534 A1 | 11/2016 | Hawkins et al. | |
| 2016/0331389 A1 | 11/2016 | Hakala et al. | |
| 2017/0135709 A1 | 5/2017 | Nguyen et al. | |

(56) References Cited

U.S. PATENT DOCUMENTS

FOREIGN PATENT DOCUMENTS

| | | | |
|---|---|---|---|
| CN | 102271748 A | | 12/2011 |
| CN | 102355856 A | | 2/2012 |
| CN | 102765785 A | | 11/2012 |
| CN | 203564304 | † | 4/2014 |
| DE | 3038445 A1 | | 5/1982 |
| DE | 202006014285 U1 | | 12/2006 |
| EP | 0442199 A2 | | 8/1991 |
| EP | 0571306 A1 | | 11/1993 |
| EP | 0647435 A1 | | 4/1995 |
| JP | 62-275446 A | | 11/1987 |
| JP | 6-125915 A | | 5/1994 |
| JP | 7-47135 A | | 2/1995 |
| JP | 10-99444 A | | 4/1998 |
| JP | 10-513379 A | | 12/1998 |
| JP | 2002-538932 A | | 11/2002 |
| JP | 2004-81374 A | | 3/2004 |
| JP | 2005-501597 A | | 1/2005 |
| JP | 2005-95410 A | | 4/2005 |
| JP | 2005-515825 A | | 6/2005 |
| JP | 2006-516465 A | | 7/2006 |
| JP | 2007-532182 A | | 11/2007 |
| JP | 2011-524203 A | | 9/2011 |
| JP | 2012-508042 A | | 4/2012 |
| WO | 1996/024297 A1 | | 8/1996 |
| WO | 1999/000060 A1 | | 1/1999 |
| WO | 1999/02096 A1 | | 1/1999 |
| WO | 2000/056237 A2 | | 9/2000 |
| WO | 2004/069072 A2 | | 8/2004 |
| WO | 2005/099594 A1 | | 10/2005 |
| WO | 2006/127158 A2 | | 11/2006 |
| WO | 2007/149905 A2 | | 12/2007 |
| WO | 2009/121017 A1 | | 10/2009 |
| WO | 2009/152352 A2 | | 12/2009 |
| WO | 2010/014515 A2 | | 2/2010 |
| WO | 2011/094111 A2 | | 8/2011 |
| WO | 2011/143468 A2 | | 11/2011 |
| WO | 2012/025833 A2 | | 3/2012 |
| WO | 2013/059735 A1 | | 4/2013 |
| WO | 2014/025397 A1 | | 2/2014 |
| WO | 2015/017499 A1 | | 2/2015 |

OTHER PUBLICATIONS

Advisory Action received for U.S. Appl. No. 12/482,995, dated Sep. 29, 2011, 2 pages.
Advisory Action received for U.S. Appl. No. 12/581,295, dated Jul. 3, 2014, 3 pages.
Advisory Action received for U.S. Appl. No. 13/049,199, dated Jun. 7, 2012, 3 pages.
Advisory Action received for U.S. Appl. No. 13/267,383, dated Jan. 6, 2014, 4 pages.
Advisory Action received for U.S. Appl. No. 13/615,107, dated Nov. 6, 2015, 3 pages.
Cleveland et al., "The Physics of Shock Wave Lithotripsy", Extracorporeal Shock Wave Lithotripsy, Part IV, Chapter 38, 2012, pp. 317-332.
Connors et al., "Renal Nerves Mediate Changes in Contralateral Renal Blood Flow after Extracorporeal Shockwave Lithotripsy", Nephron Physiology, vol. 95, 2003, pp. 67-75.
Decision to Grant received for European Patent Application No. 13756766.5, dated May 27, 2016, 2 pages.
Decision to Grant received for Japanese Patent Application No. 2011-513694, dated Oct. 7, 2014, 3 pages (Official Copy Only) (See Communication under 37 CFR § 1.98(a) (3)).
Extended European Search Report (includes Supplementary European Search Report and Search Opinion) received for European Patent Application No. 09763640.1, dated Oct. 10, 2013, 5 pages.
Extended European Search Report received for European Patent Application No. 13827971.6, dated Apr. 12, 2016, 8 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 13/049,199 dated Aug. 11, 2014, 8 pages.
Final Office Action received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107, dated Sep. 1, 2015, 9 pages.
Final Office Action received for U.S. Appl. No. 13/646,570, dated Dec. 23, 2014, 10 pages.
Final Office Action received for U.S. Appl. No. 14/271,342, dated Feb. 27, 2015, 7 pages.
Gambihler et al., "Permeabilization of the Plasma Membrane of L1210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Current Hypertension Reports, vol. 14, 2012, pp. 567-572.
Intention to Grant received for European Patent Application No. 13756766.5, dated Jan. 8, 2016, 5 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987, dated Nov. 20, 2014, 11 pages.
International Preliminary Report on Patentability received for PCT Patent Application No. PCT/US2013/048277, dated Jan. 8, 2015, 9 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533, dated Mar. 26, 2015, 10 pages.
International Preliminary Report on Patentability received for PCT Patent Application No. PCT/US2012/063925, dated May 22, 2014, 12 pages.
International Search Report and Written Opinion received for PCT Patent Application No. PCT/US2013/031805, dated May 20, 2013, 13 pages.
International Search Report and Written Opinion received for PCT Patent Application No. PCT/US2016/060817, dated Feb. 20, 2017, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.

(56) References Cited

OTHER PUBLICATIONS

International Search Report and Written Opinion received for PCT Patent Application No. PCT/US2015/029088, dated Jul. 16, 2015, 13 pages.
International Search Report received for PCT Patent Application No. PCT/US2009/047070, dated Jan. 19, 2010, 4 pages.
International Search Report received for PCT Patent Application No. PCT/US2012/023172, dated Sep. 28, 2012, 3 pages.
International Written Opinion received for PCT Patent Application No. PCT/US2009/047070, dated Jan. 19, 2010, 5 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
Kodama et al., "Shock Wave-Mediated Molecular Delivery into Cells", Biochimica et Biophysica Acta., vol. 1542, 2002, pp. 186-194.
Lauer et al., "Shock Wave Permeabilization as a New Gene Transfer Method", Gene Therapy, vol. 4, 1997, pp. 710-715.
Non-Final Office Action received for U.S. Appl. No. 12/482,995, dated Aug. 13, 2014, 10 pages.
Non-Final Office Action received for U.S. Appl. No. 12/482,995, dated Jul. 12, 2013, 11 pages.
Non-Final Office Action received for U.S. Appl. No. 13/465,264, dated Oct. 29, 2014, 13 pages.
Non-Final Office Action received for U.S. Appl. No. 13/534,658, dated Mar. 11, 2016, 12 pages.
Non-Final Office Action received for U.S. Appl. No. 13/646,570, dated Oct. 29, 2014, 10 pages.
Non-Final Office Action received for U.S. Appl. No. 14/079,463, dated Mar. 4, 2014, 9 pages.
Non-Final Office Action received for U.S. Appl. No. 14/218,858, dated Mar. 30, 2016, 13 pages.
Non-Final Office Action received for U.S. Appl. No. 14/515,130, dated Jan. 14, 2016, 16 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 13/049,199, dated Feb. 4, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 15/474,885, dated Oct. 5, 2017, 9 pages.
Non-Final Office Action received for U.S. Appl. No. 14/273,063, dated Jun. 3, 2016, 9 pages.
Non-Final Office Action received for U.S. Appl. No. 12/611,997, dated Nov. 26, 2014, 8 pages.
Notice of Acceptance received for Australian Patent Application No. 2009257368, dated Aug. 28, 2014, 2 pages.
Notice of Allowance received for Japanese Patent Application No. 2015-520522, dated Feb. 23, 2017, 3 pages (Official Copy Only) (See Communication under 37 CFR § 1.98(a) (3)).
Notice of Allowance received for Chinese Patent Application No. 201380033808.3, dated Dec. 29, 2016, 4 pages (Official Copy Only) (See Communication under 37 CFR § 1.98(a) (3)).
Notice of Allowance received for Chinese Patent Application No. 201380041656.1, dated Mar. 3, 2017, 4 pages (Official Copy Only) (See Communication under 37 CFR § 1.98(a) (3)).
Notice of Allowance received for U.S. Appl. No. 14/515,130, dated May 2, 2016, 8 pages.
Notice of Allowance received for Canadian Patent Application No. 2,727,429, dated May 26, 2015, 1 page.
Notice of Allowance received for U.S. Appl. No. 15/474,885, dated Feb. 14, 2018, 5 pages.
Notice of Allowance received for U.S. Appl. No. 12/482,995, dated Dec. 24, 2014, 6 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/465,264, dated May 8, 2015, 7 pages.
Notice of Allowance received for U.S. Appl. No. 13/534,658, dated Jan. 5, 2017, 6 pages.
Notice of Allowance received for U.S. Appl. No. 13/534,658, dated Jan. 18, 2017, 4 pages.
Notice of Allowance received for U.S. Appl. No. 13/615,107, dated Dec. 31, 2015, 10 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 13/957,276, dated Aug. 28, 2015, 9 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,276, dated Feb. 25, 2015, 8 pages.
Notice of Allowance received for U.S. Appl. No. 14/271,342, dated Mar. 13, 2015, 5 pages.
Notice of Allowance received for U.S. Appl. No. 14/515,130, dated May 25, 2016, 3 pages.
Office Action received for Australian Patent Application No. 2013284490, dated Jun. 5, 2017, 4 pages.
Office Action received for Australian Patent Application No. 2013300176, dated Nov. 10, 2016, 2 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Canadian Patent Application No. 2,727,429, dated Apr. 14, 2015, 4 pages.
Office Action received for Chinese Patent Application No. 201380033808.3, dated Jul. 5, 2016, 9 pages (3 pages of English Translation and 6 pages of Official Copy).
Office Action received for Chinese Patent Application No. 201380041656.1, dated Jul. 5, 2016, 9 pages (4 pages of English Translation and 5 pages of Official Copy).
Office Action received for Chinese Patent Application No. 201380042887.4, dated Aug. 8, 2016, 9 pages (4 pages of English Translation and 5 pages of Official Copy).
Office Action received for Japanese Patent Application No. 2015-526523, dated Jan. 25, 2017, 8 pages (5 pages of English Translation and 3 pages of Official Copy).

(56) References Cited

OTHER PUBLICATIONS

Office Action received for Japanese Patent Application No. 2011-513694, dated Aug. 27, 2013, 6 pages (2 pages of English Translation and 6 pages of Official Copy).
Office Action received for Japanese Patent Application No. 2011-513694, dated Jun. 10, 2014, 4 pages (2 pages of English Translation and 2 pages of Official Copy).
Office Action received for Japanese Patent Application No. 2014-158517, dated May 19, 2015, 5 pages (2 pages of English Translation and 3 pages of Official Copy).
Office Action Received for Japanese Patent Application No. 2011-534914, dated Jul. 15, 2014, 3 pages (1 page of English Translation and 2 pages of Official Copy).
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electrohydraulic Lithotripsy", Journal of Endourology, vol. 11, No. 1, Feb. 1997, pp. 55-61.
International Search Report and Written Opinion Received for PCT Application No. PCT/US2018/059083, dated Jan. 22, 2019, 10 pages.

† cited by third party

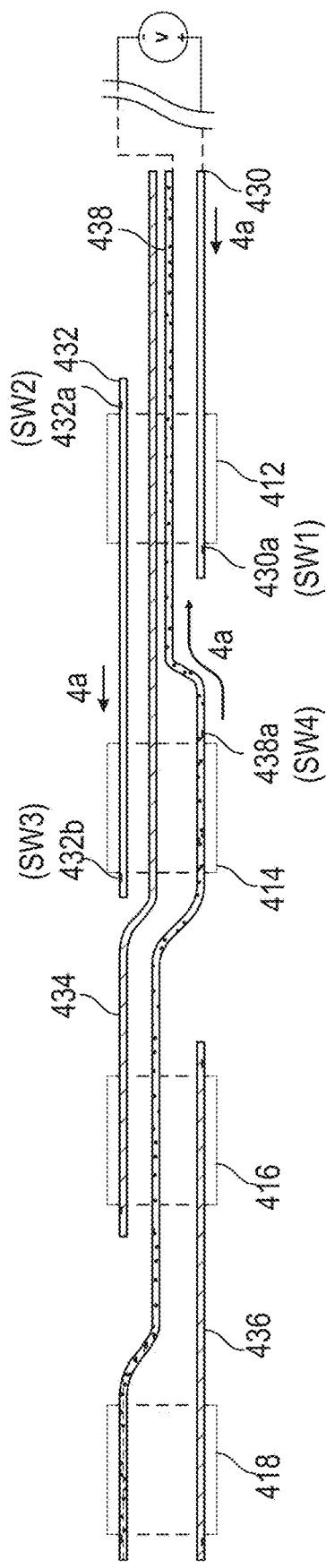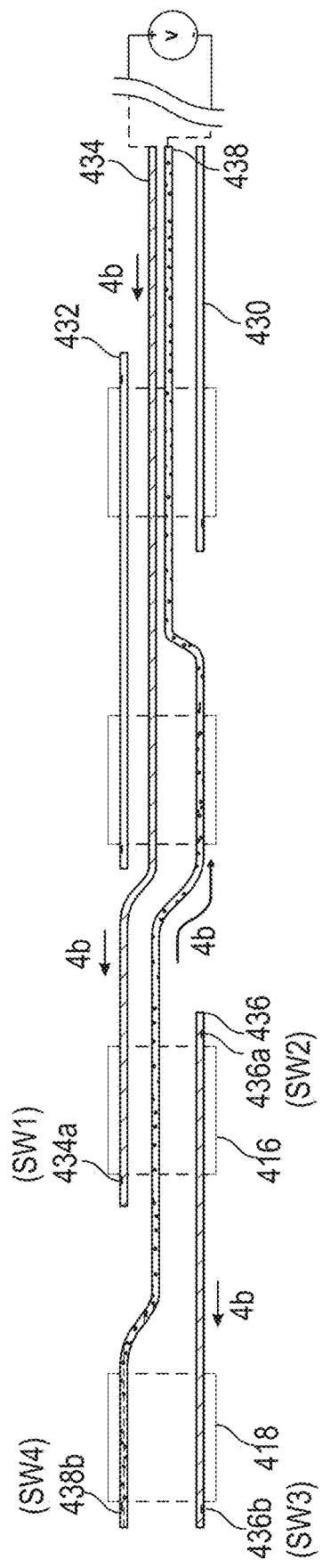
FIG. 4C
FIG. 4D

LOW PROFILE ELECTRODES FOR A SHOCK WAVE CATHETER

The present disclosure relates generally to shock wave electrodes, and more specifically, to electrodes for the generation of shock waves within vascular structures.

BACKGROUND

The present invention relates to a treatment system for percutaneous coronary angioplasty or peripheral angioplasty in which an angioplasty balloon is used to dilate a lesion (e.g., calcified lesion) and restore normal blood flow in the artery. In this type of procedure, a catheter carrying a balloon is advanced into the vasculature along a guide wire until the balloon is aligned with calcified plaques. The balloon is then pressurized to reduce or break the calcified plaques and push them back into the vessel wall.

More recently, the assignee herein has developed a treatment system that includes electrodes within an angioplasty type balloon. In use, the balloon is advanced to the region of an occlusion. The balloon is then partially pressurized with a conductive fluid. A series of high voltage pulses are applied to the electrodes within the balloon, with each pulse generating a shock wave in the conductive fluid. The shock waves pass through the balloon wall and into the occlusion, cracking the calcified plaques. Once the calcified plaques are cracked, the balloon can be further expanded to open the vessel. Such system is disclosed in U.S. Pat. Nos. 8,956,371 and 8,888,788, both of which are incorporated herein by reference. Further, the assignee herein has developed techniques for providing an electrode on the tip of a guide wire for generating forward directed shock waves. This approach is disclosed in U.S. Patent Publication No. 2015/0320432, also incorporated herein by reference.

The present invention relates to yet another alternative for placing shock wave electrodes near an occlusion. This approach can be used along or in conjunction with an angioplasty balloon.

BRIEF SUMMARY

The invention provides a device for generating shock waves. In some embodiments, the device comprises an elongated tube and a conductive sheath circumferentially mounted around the elongated tube. The device further comprises a first insulated wire extending along the outer surface of the elongated tube and a second insulated wire extending along the outer surface of the elongated tube. A portion of the first insulated wire is removed to form a first inner electrode and the first inner electrode is adjacent to a first side edge of the conductive sheath. A portion of the second insulated wire is removed to form a second inner electrode and the second inner electrode is adjacent to a second side edge of the conductive sheath. When a high voltage is applied across the first inner electrode and the second inner electrode, a current is configured to flow from the first wire to the first side edge of the conductive sheath and from the second side edge of the conductive sheath to the second wire. A first shock wave is created across the first side edge of the conductive sheath and the first inner electrode, and a second shock wave is created across the second side edge of the conductive sheath and the second inner electrode.

In some embodiments, the device comprises an elongated tube and three conductive sheaths each circumferentially mounted around the elongated tube. The device further comprises a first insulated wire, a second insulated wire, a third insulated wire, and an insulated common ground wire, each extending along the outer surface of the elongated tube. A portion of the first insulated wire is removed to form a first inner electrode; two portions of the second insulated wire are removed to form a second inner electrode and a third inner electrode; two portions of the third insulated wire are removed to form a fourth inner electrode and a fifth inner electrode; a portion of the insulated common ground wire is removed to form a sixth inner electrode. When a high voltage is applied across the first wire and the insulated common ground wire, a current is configured to flow from the first wire to a first side edge of the first conductive sheath, from a second side edge of the first conductive sheath to the second wire, from the second wire to a first side edge of the second conductive sheath, from a second side edge of the second conductive sheath to the third wire, from the third wire to a first side edge of the third conductive sheath, from a second side edge of the third conductive sheath to the insulated common ground wire. Accordingly, a first shock wave is created across the first side edge of the first conductive sheath and the first inner electrode, a second shock wave is created across the second side edge of the first conductive sheath and the second inner electrode, a third shock wave is created across the first side edge of the second conductive sheath and the third inner electrode, a fourth shock wave is created across the second side edge of the second conductive sheath and the fourth inner electrode, a fifth shock wave is created across the first side edge of the third conductive sheath and the fifth inner electrode, and a sixth shock wave is created across the second side edge of the third conductive sheath and the sixth inner electrode.

In some embodiments, a device for generating shock waves comprises an elongated tube and four conductive sheaths each circumferentially mounted around the elongated tube. The device further comprises a first insulated wire, a second insulated wire, a third insulated wire, a fourth insulated wire, and an insulated common ground wire, each extending along the outer surface of the elongated tube. A portion of the first insulated wire is removed to form a first inner electrode; two portions of the second insulated wire are removed to form a second inner electrode and a third inner electrode; a portion of the third insulated wire is removed to form a fifth inner electrode; two portions of the fourth insulated wire are removed to form a sixth inner electrode and a seventh inner electrode; two portions of the insulated common ground wire are removed to form a fourth inner electrode and an eighth inner electrode. When a high voltage is applied across the first wire and the insulated common ground wire, a first current is configured to flow from the first wire to a first side edge of the first conductive sheath to generate a first shock wave across the first side edge of the first conductive sheath and the first inner electrode, from a second side edge of the first conductive sheath to the second wire to generate a second shock wave across the second side edge of the first conductive sheath and the second inner electrode, from the second wire to a first side edge of the second conductive sheath to generate a third shock wave across the first side edge of the second conductive sheath and the third inner electrode, from a second side edge of the second conductive sheath to the insulated common ground wire to generate a fourth shock wave across the second side edge of the second conductive sheath and the fourth inner electrode. When a high voltage is applied across the third wire and the insulated common ground wire, a second current is configured to flow from the third insulated wire to a first side edge of the third conductive sheath to generate a fifth shock wave across the first side edge of the third conductive sheath and the fifth inner electrode, from a second side edge of the third conductive sheath to the fourth insulated wire to generate a sixth shock wave across the second side edge of the third conductive sheath and the sixth inner electrode, from the fourth insulated wire to a first side edge of the fourth conductive sheath to generate a seventh shock wave across the first side edge of the fourth conductive sheath and the seventh inner electrode, and from a second side edge of the fourth conductive sheath to the insulated common ground wire to generate an eighth shock wave across the second side edge of the fourth conductive sheath and the eighth inner electrode.

DESCRIPTION OF THE FIGURES

FIG. 4C schematically depicts an electrical diagram of the configuration of FIG. 4A, in accordance with some embodiments.

FIG. 4D schematically depicts an electrical diagram of the configuration of FIG. 4A, in accordance with some embodiments.

DETAILED DESCRIPTION

Figure 1:
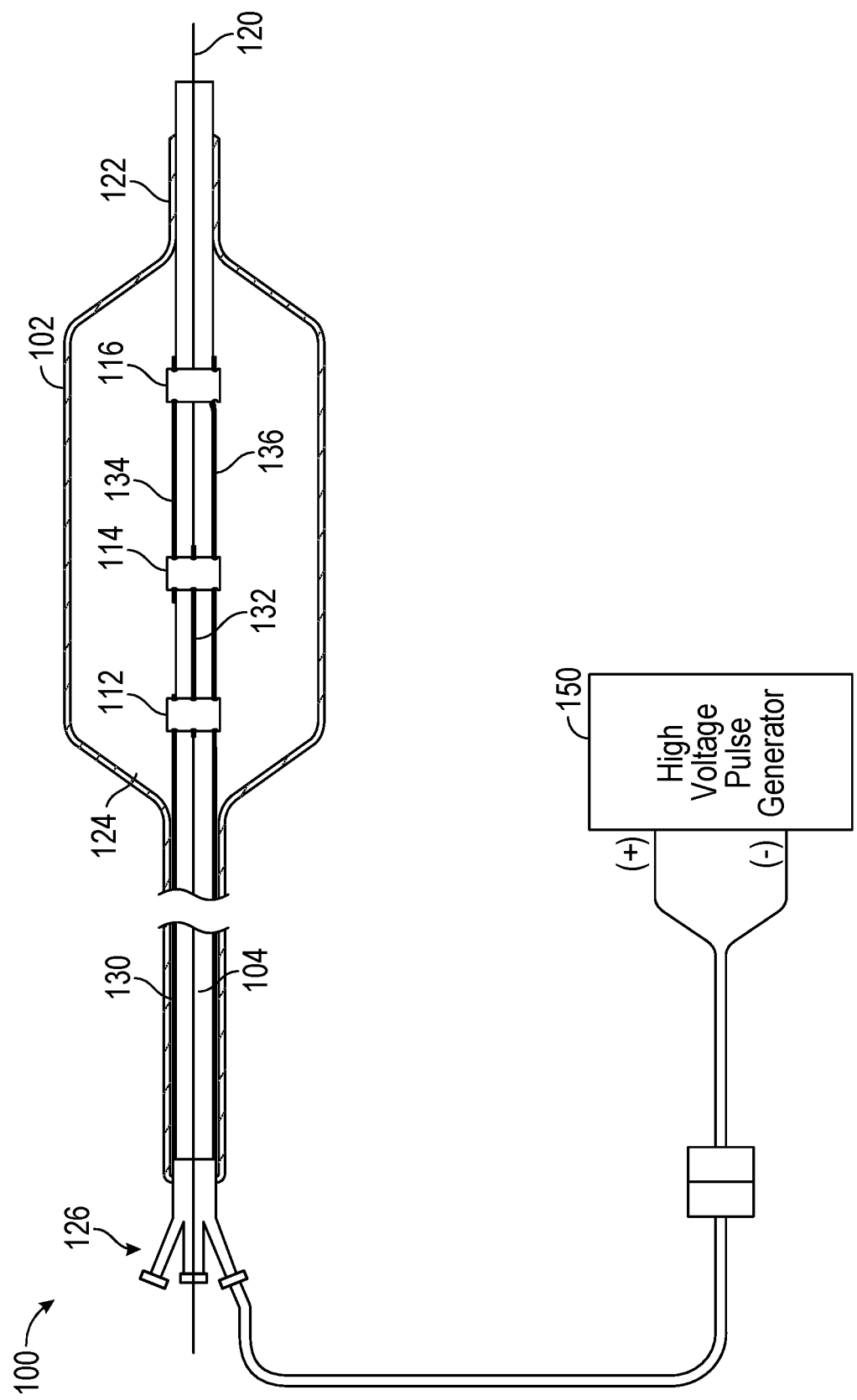
FIG. 1 depicts an exemplary shock wave angioplasty device having a plurality of electrode assemblies, in accordance with some embodiments.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The assignee herein has developed a number of low-profile shock wave electrodes that may be suitable for use in angioplasty and/or valvuloplasty procedures. For example, in U.S. Pat. No. 8,888,788, the assignee discloses a low-profile electrode assembly comprising an inner electrode, an insulating layer overlaying the inner electrode, and an outer electrode. The outer electrode may be a conductive sheath having a central opening that is coaxially aligned with an opening in the insulating layer. In operation, plasma arcs can be formed across the inner electrode and the opening in the outer electrode to generate shock waves. The above-described design reduces the crossing-profile of the shock wave device because the inner electrode, the outer electrode, and the insulating layer are stacked, thus allowing the shock wave device to easily navigate through, access, and treat target vascular tissues.

In operation, the plasma arcs generated across the inner electrode and the outer electrode cause erosion in the conductive sheath, resulting in widening of the opening in both directions. As the opening widens, it becomes more difficult to control the generation, location, and/or magnitude of plasma arcs (and therefore shock waves), thus negatively impacting the longevity of the electrode assembly.

Described herein are shock wave electrode assemblies that are designed to be low-profile and durable. In some embodiments, an outer electrode is formed by a conductive sheath without an opening on the outer surface, and an inner electrode is formed by removing a portion of an insulated wire (e.g., cutting a hole in the insulating layer near the end of the wire) to expose an electrically conductive portion of the insulated wire. The inner electrode is placed a controlled distance apart from the side edge of the conductive sheath to allow for a reproducible arc for a given current and voltage. In operation, plasma arcs may be formed across the inner electrode and the side edge of the conductive sheath, rather than across the inner electrode and an opening of the sheath. As such, the plasma arcs would cause erosion only in the one direction into the side edge, rather than causing erosion in both directions to widen the opening in the previous designs. Thus, the longevity of the electrode assembly is effectively doubled. Additionally, the present design eliminates the use of an insulated layer stacked between the inner electrode and the outer electrode, thus further reducing the crossing-profile of the device. In some embodiments, the inner electrode is formed by cutting the end of the insulated wire to expose an electrically conductive cross-section of the wire, and the end of the insulated wire is placed a controlled distance from the side edge of the conductive sheath as described above to form the electrode assembly. The assembling process is significantly easier than stacking the electrodes and aligning the opening of the conductive sheath with the opening of the insulating layer as required by previous designs, thus reducing manufacture cost and improving the usability and effectiveness of the shock wave device.

FIG. 1 depicts an exemplary shock wave angioplasty device 100 according to an embodiment of the invention. The shock wave device 100 includes an elongated tube 104 and an angioplasty balloon 102. The angioplasty balloon wraps circumferentially around a portion of the elongated tube 104 in a sealed configuration via, for example, a seal 122. The angioplasty balloon 102 forms an annular channel 124 around the elongated tube 104 through which a conductive fluid, such as saline, may be admitted into the balloon via fill ports 126. The balloon is filled with the fluid such that the balloon can be inflated and gently fixed to the walls of the artery in direct proximity with a calcified lesion. In some embodiments, the fluid may also contain an x-ray contrast to permit fluoroscopic viewing of the catheter during use.

The elongated tube 104 includes a number of longitudinal grooves or channels configured for retaining wires and/or inner electrodes. In the depicted example in FIG. 1, the elongated tube 104 has four grooves along the length of the elongated tube. Insulated wires 130, 132, 134, and 136 are placed within the grooves of the elongated tube 104. Furthermore, a number of conductive sheaths 112, 114, and 116 are circumferentially mounted around the elongated tube 104. A variable high voltage pulse generator 150 is connected to the insulated wire 130 and the insulated wire 136. The insulated wires and the sheaths form three electrode assemblies that can be activated to generate shock waves at 6 locations (e.g., along the length of the vessel), as discussed in detail below. The elongated tube 104 also includes a lumen through which a guide wire 120 is inserted.

In operation, a physician uses the guidewire 120 to guide the elongated tube 104 into position. Once positioned, the variable high voltage pulse generator 150 is used to deliver a series of pulses to create a series of shock waves within the angioplasty balloon 102 and within the artery being treated. The magnitude of the shock waves can be controlled by controlling the magnitude of the pulsed voltage, the current, the duration, and the repetition rate. The physician may start with low energy shock waves and increase the energy as needed to crack the calcified plaques. Such shock waves will be conducted through the fluid, through the balloon, through the blood and vessel wall to the calcified lesion where the energy will break the hardened plaque.

Figure 2A:
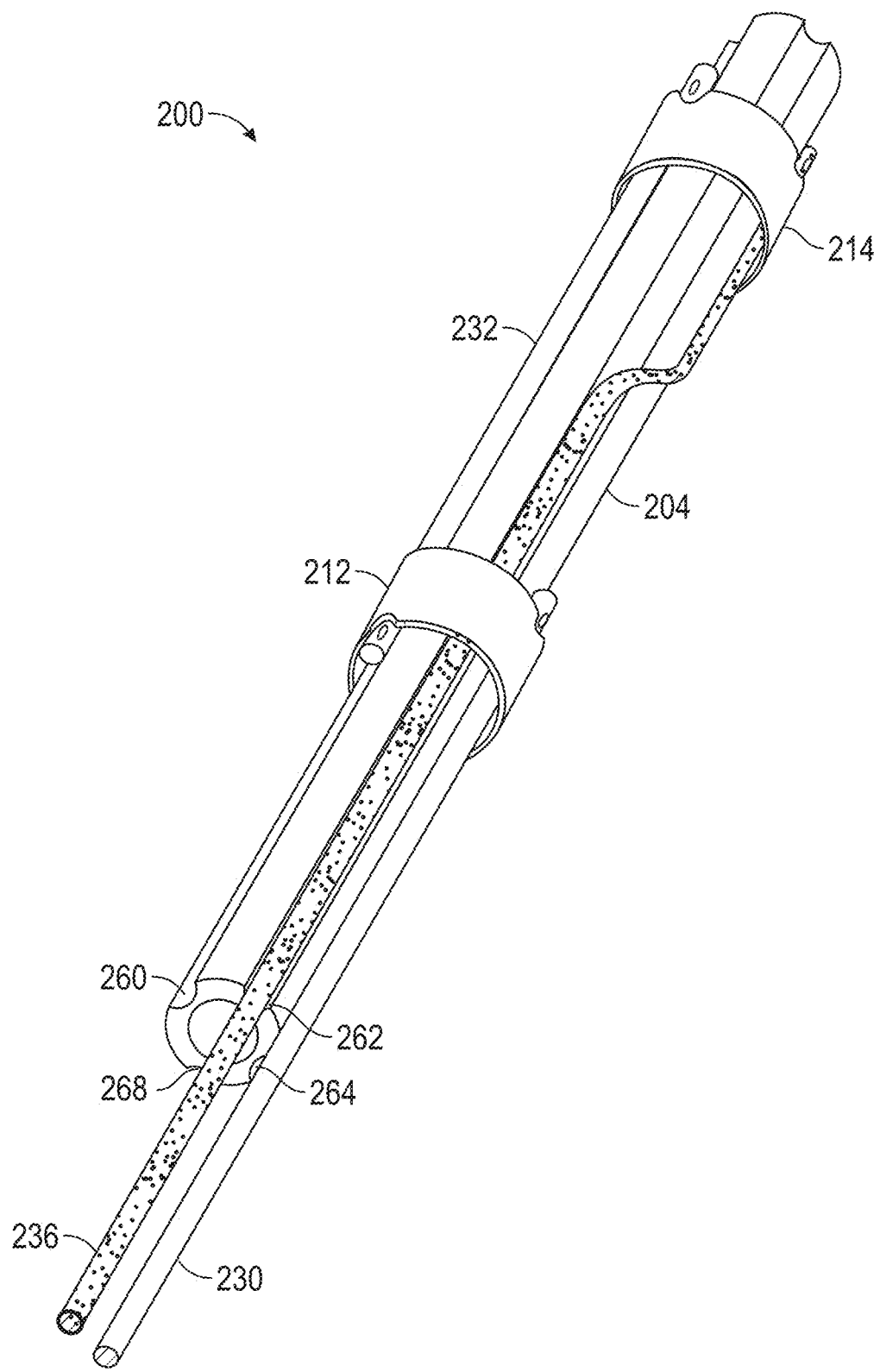
FIG. 2A depicts a set of shock wave electrode assemblies in an exemplary shock wave angioplasty device that may be activated to generate shock waves at 4 locations, in accordance with some embodiments.

FIG. 2A depicts a plurality of shock wave electrode assemblies that may be included in an exemplary shock wave angioplasty device such as the device depicted in FIG. 1. As depicted, the shock wave angioplasty device 200 includes an elongated tube 204 having four longitudinal grooves 260, 262, 264, and 268. A number of insulated wires 230, 232, and 236 are disposed on the outer surface of the elongated tube 204 such that they extend along the length of the elongated tube. As depicted, the insulated wire 230 is disposed in the groove 264 and the insulated wire 232 is disposed in the groove 260. The insulated wire 236 has a first straight portion disposed in the groove 262, a second straight portion disposed in the groove 264, and a curved portion disposed between the grooves 262 and 264.

Figure 2B:
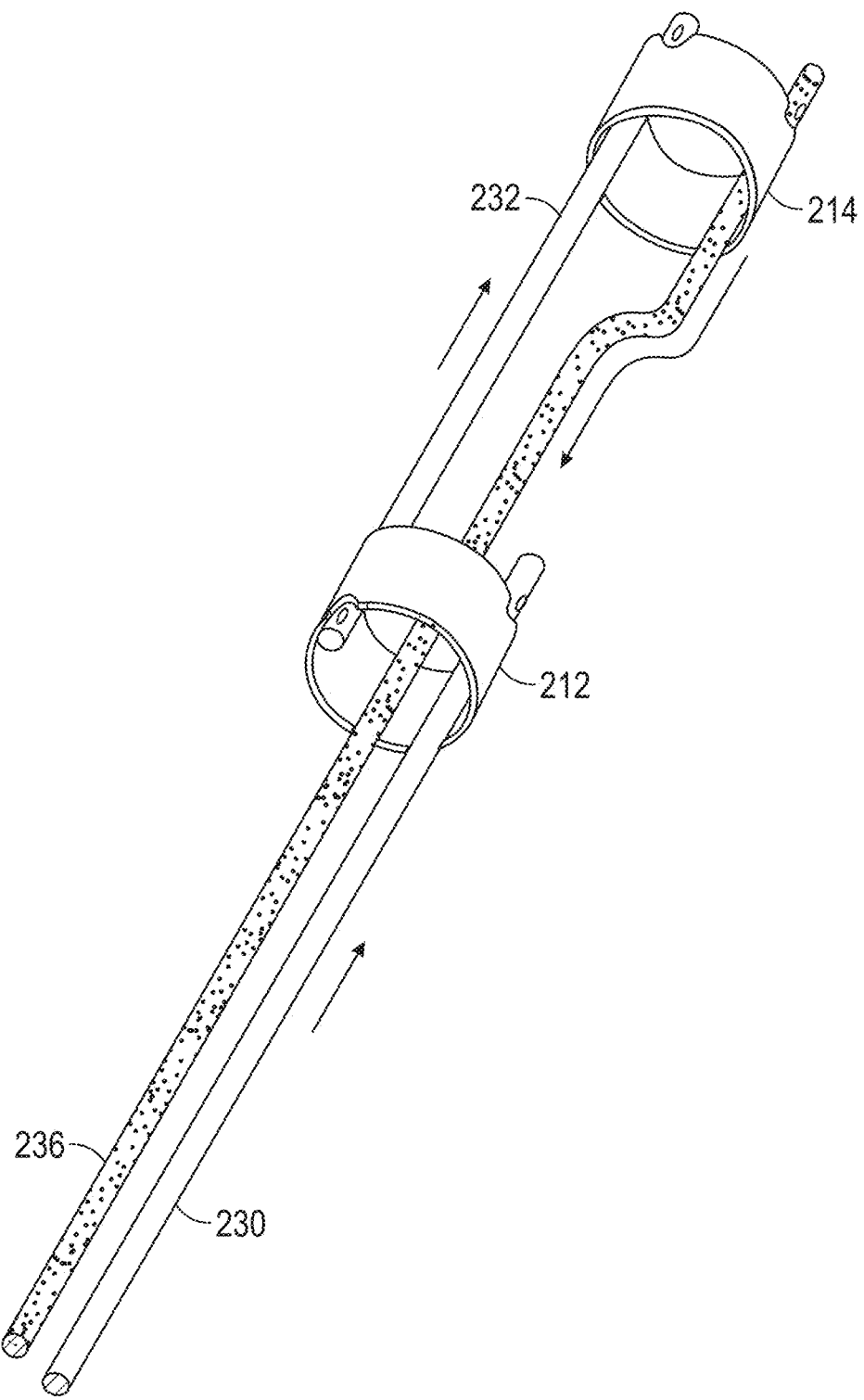
FIG. 2B depicts the connectivity between a plurality of inner electrodes and sheaths to attain the configuration of FIG. 2A, in accordance with some embodiments.

The shock wave angioplasty device 200 further includes a first conductive sheath 212 and a second conductive sheath 214 each circumferentially mounted around the elongated tube 204. As depicted in FIGS. 2A and 2B, the length of the first conductive sheath 212 overlaps with and covers a portion of the insulated wire 230 near its distal end, a portion of the insulated wire 232 near its proximal end, and a portion of the insulated wire 236. The length of the second conductive sheath 214 overlaps with and covers a portion of the insulated wire 232 near its distal end and a portion of the insulated wire 236 near its distal end.

Figure 2C:
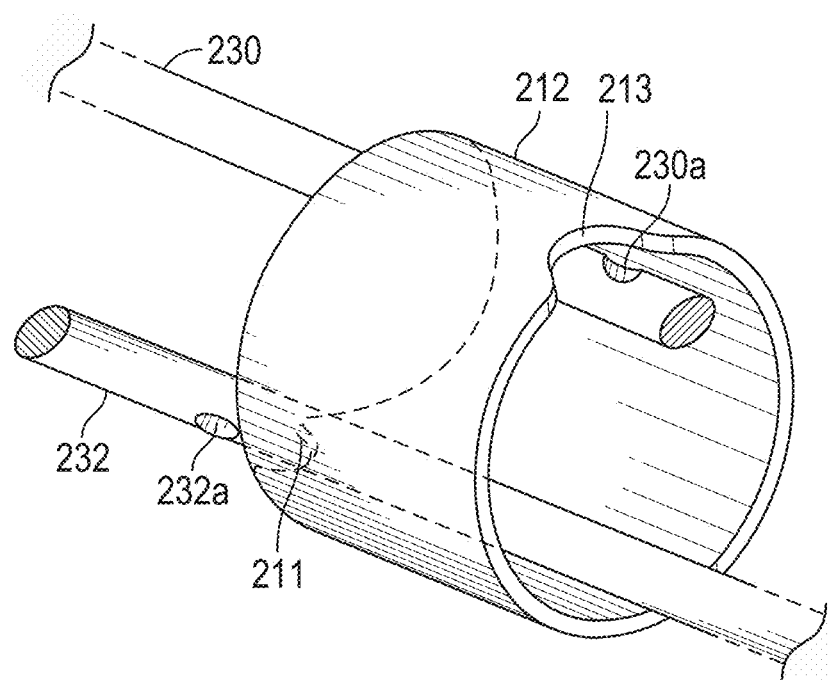
FIG. 2C depicts an exemplary electrode assembly, in accordance with some embodiments.

The electrode assemblies of the shock wave angioplasty device 200 are described below with reference to FIGS. 2C and 2D. Turning to FIG. 2C, a portion of the insulating layer of the wire 230 is removed near the distal end of the wire 230 to expose an electrically conductive wire portion, forming the first inner electrode 230a. In the depicted example, a hole in the insulating layer is cut on the curved outer surface along the length of the wire. The removed portion may be in any shape, such as a circle, a rectangle, a strip around the circumference of the wire, etc. The location, shape, and size of the removed portion may vary to control the location, direction, and/or magnitude of the shock wave. In some embodiments, an inner electrode may be formed by cutting the end of the wire to expose an electrically conductive cross-section of the wire. In some embodiments, flat wires rather than round wires are used to further reduce the crossing profile of the electrode assembly.

As shown in FIG. 2C, the first inner electrode 230a is adjacent to, but not in contact with, a distal side edge 213 of the first conductive sheath 212. The first conductive sheath 212 functions as an outer electrode, and the first inner electrode 230a is placed a controlled distance apart from the distal side edge 213 of the first conductive sheath to allow for a reproducible arc for a given voltage and current. The electrical arcs are then used to generate shock waves in the conductive fluid. In operation, a first shock wave is created across the first inner electrode 230a and the distal side edge 213 of the first conductive sheath 212, the details of which are provided below with reference to FIG. 2E.

In a similar manner, a portion of the insulated wire 232 is removed to form a second inner electrode 232a. Specifically, a portion of the insulating layer of the wire 232 is removed near the proximal end of the wire 232 to expose an electrically conductive wire portion along the length of the wire, forming the second inner electrode 232a. As shown, the second inner electrode 232a is adjacent to, but not in contact with, a proximal side edge 211 of the first conductive sheath 212. Further, the first inner electrode 230a and the second inner electrode 232a are positioned circumferentially 180 degrees from each other. In operation, the first conductive sheath 212 acts as an outer electrode and a second shock wave is created across the second inner electrode 232a and the proximal side edge 211 of the first conductive sheath 212, the details of which are provided below with reference to FIG. 2E.

Figure 2D:
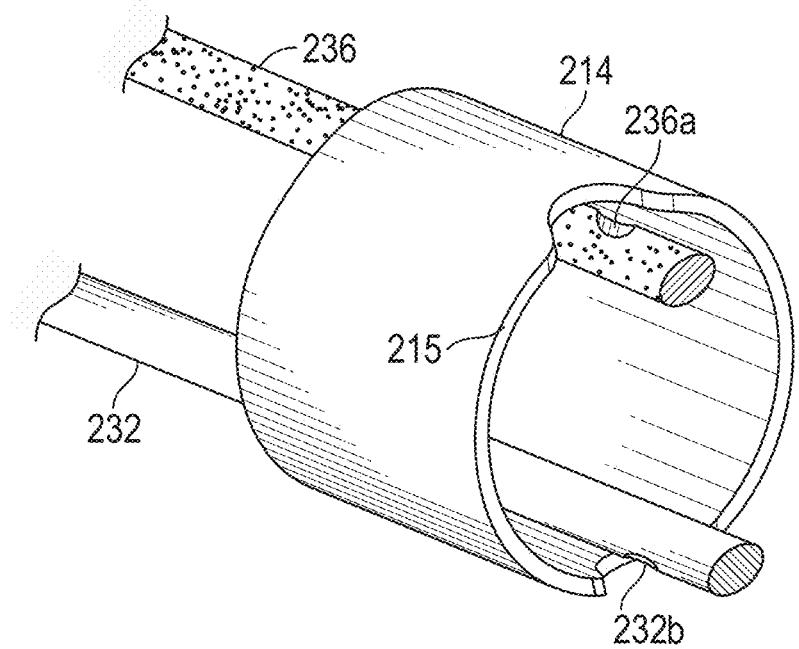
FIG. 2D depicts an exemplary electrode assembly, in accordance with some embodiments.

Turning to FIG. 2D, a third inner electrode 232b is formed on the insulated wire 232 and a fourth inner electrode 236a is formed on the insulated wire 236 in a similar manner as described above with reference to FIG. 2C. As depicted, the third inner electrode 232b is formed near the distal end of the insulated wire 232 and is adjacent to, but not in contact with, a distal side edge 215 of the second conductive sheath 214. The fourth inner electrode 236a is formed near the distal end of the insulated wire 236 and is adjacent to, but not in contact with, the same distal side edge 215 of the second conductive sheath 214. In operation, the second conductive sheath 214 acts as an outer electrode, a third shock wave is created across the third electrode 232b and the distal side edge 215 and a fourth shock wave is created across the fourth electrode 236a and the distal side edge 215, the details of which are provided below with reference to FIG. 2E.

In the depicted example in FIGS. 2C and 2D, the first conductive sheath 212 includes a first arcuate cut-out on the distal side edge 213, and the first inner electrode 230a is positioned adjacent to the first arcuate cut-out such that the first shock wave is created across the first arcuate cut-out and the first inner electrode. Further, the first conductive sheath 212 includes a second arcuate cut-out on the proximal side edge 211 positioned circumferentially 180 degrees from the first cut-out, and the second inner electrode 232a is positioned adjacent to the second arcuate cut-out such that the second shock wave is created across the second arcuate cut-out and the second inner electrode. The cut-outs on the conductive sheath allow the inner electrodes to be placed closer to the sheath without coming into direct contact with the sheath, and also allows for better control of the locations of the shock waves and more predictable and even wear on the conductive sheath. It should be appreciated by one of ordinary skill in the art that a shock wave can be generated between an inner electrode and a straight side edge of the conductive sheath that does not include any cut-outs.

Figure 2E:
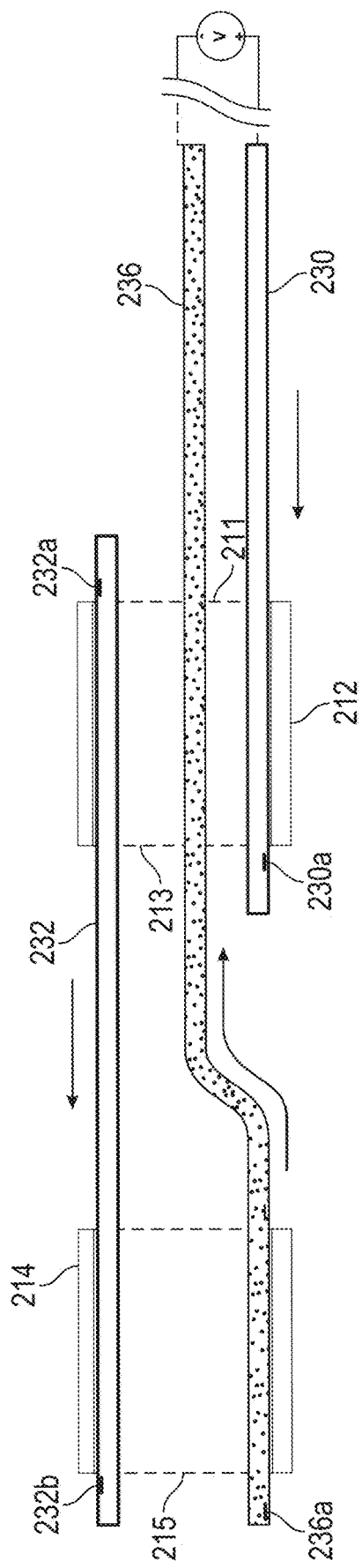
FIG. 2E schematically depicts an electrical diagram of the configuration of FIG. 2A, in accordance with some embodiments.

FIG. 2E schematically depicts an electrical diagram of the configuration of FIGS. 2A-D, in accordance with some embodiments. When a high voltage is applied (e.g., using the high voltage pulse generator 150 of FIG. 1) across the proximal end of the insulated wire 230 and the proximal end of the insulated wire 236, a current may flow as indicated by the arrows, with the insulated wire 236 as the common ground wire (i.e., connecting to a ground or negative channel). As shown, the current flows from the proximal end of the insulated wire 230 toward to the distal end of the insulated wire 230 and, via the insulation removed spot that is electrically conductive (i.e., the first inner electrode 230a), to the distal side edge 213 of the first conductive sheath 212 (i.e., the first outer electrode). The duration and the magnitude of the voltage pulse are set to be sufficient to generate a gas bubble at the surface of the first inner electrode 230a causing a plasma arc of electric current to traverse the bubble and create a rapidly expanding and collapsing bubble, which creates the mechanical shock wave in the balloon. The size of the bubble and the rate of expansion and collapse of the bubble (and therefore the magnitude, duration, and distribution of the mechanical force) may vary based on the magnitude and duration of the voltage pulse, as well as the distance between the inner and outer electrodes, the surface area of the electrodes, and/or the shape of the outer electrode (e.g., whether there is an arcuate cut-out on the side edge).

The current may further traverse from the proximal side edge 211 of the first conductive sheath 212 (i.e., the first outer electrode) to the insulated wire 232, via the insulation removed spot near the proximal end of the insulated wire 232 (i.e., the second inner electrode 232a). The voltage pulse may create a potential difference between the first outer electrode and the second inner electrode high enough to form a plasma arc between them, generating a bubble that gives rise to a second shock wave. In the depicted example, the first inner electrode 230a and the second inner electrode 232a are located circumferentially opposite to each other (e.g., 180 degrees apart around the circumference of the elongated tube), and thus the first shock wave and the second shock wave may propagate in opposite directions, extending outward from the side of the elongated tube.

The current may further traverse from the proximal end of the insulated wire 232 toward to the distal end of the wire and, via the insulation removed spot that is electrically conductive near the distal end of the wire (i.e., the third inner electrode 232b), to the distal side edge 215 of the second conductive sheath 214 (i.e., the second outer electrode). The high voltage pulse generator may apply a voltage pulse such that the potential difference between the third inner electrode 232b and the second outer electrode is high enough to form a plasma arc between them, generating a bubble that gives rise to a third shock wave.

The current may further traverse from the distal side edge 215 of the second conductive sheath 214 to the insulated wire 236, via the insulation removed spot on the insulated wire 236 (i.e., the fourth inner electrode 236a). The voltage pulse may create a potential difference between the second outer electrode and the fourth inner electrode high enough to form a plasma arc between them, generating a bubble that gives rise to a fourth shock wave. The current then returns to the voltage source generator via the insulated wire 236 to a voltage output port (not depicted), which may be a negative channel or a ground channel. Optionally, a connector (not depicted) may be provided between the insulated wires 230 and 236 and the voltage pulse generator so that the wires may be easily connected to the output ports of the high voltage generator. It should be appreciated that the configuration depicted in FIG. 2E can operate as described above regardless of whether the side edges of the conductive sheaths are straight or have arcuate cut-outs.

In the embodiments depicted in FIGS. 2A-E, each electrode assembly includes a pair of inner electrodes configured to generate shock waves at two locations. For example, the electrode assembly consisting of conductive sheath 212 and inner electrodes 230a and 232a is configured to generate two shock waves via the two inner electrodes positioned circumferentially 180 degrees from each other. Further, the device 200 includes multiple electrode assemblies along the length of the elongated tube. Since the magnitude, duration, and distribution of the mechanical force impinging on a portion of tissue depends at least in part on the location and distance between the shock wave source and the tissue portion, a shock wave device having multiple shock wave electrodes at different locations (circumferentially and longitudinally) may help to provide consistent or uniform mechanical force to a region of tissue. The plurality of electrodes may be distributed across the device to minimize the distance between the shock wave source(s) and the tissue location being treated. In some embodiments, the elongated tube may be sized and shaped to distribute shock wave forces to a non-linear anatomical region (e.g., valve and/or valve leaflets). It should also be appreciated that the voltage polarity can be reversed and current flow in the opposite direction.

It should be appreciated that, in some embodiments, an electrode assembly may include a single inner electrode that is configured to generate shock wave at a single location. For example, with reference to FIG. 2E, insulated wires 232 and 236 may be removed, and a common ground wire may connect the conductive sheath 322 (e.g., the distal edge 213 of the conductive sheath) directly to the ground or negative channel of a voltage source. This way, as a current flows from the insulated wire 230 to the conductive sheath 212 to the common ground wire, a shock wave is generated at a single location (i.e., across the inner electrode 230a and the distal side edge 213 of the conductive sheath).

Figure 3A:
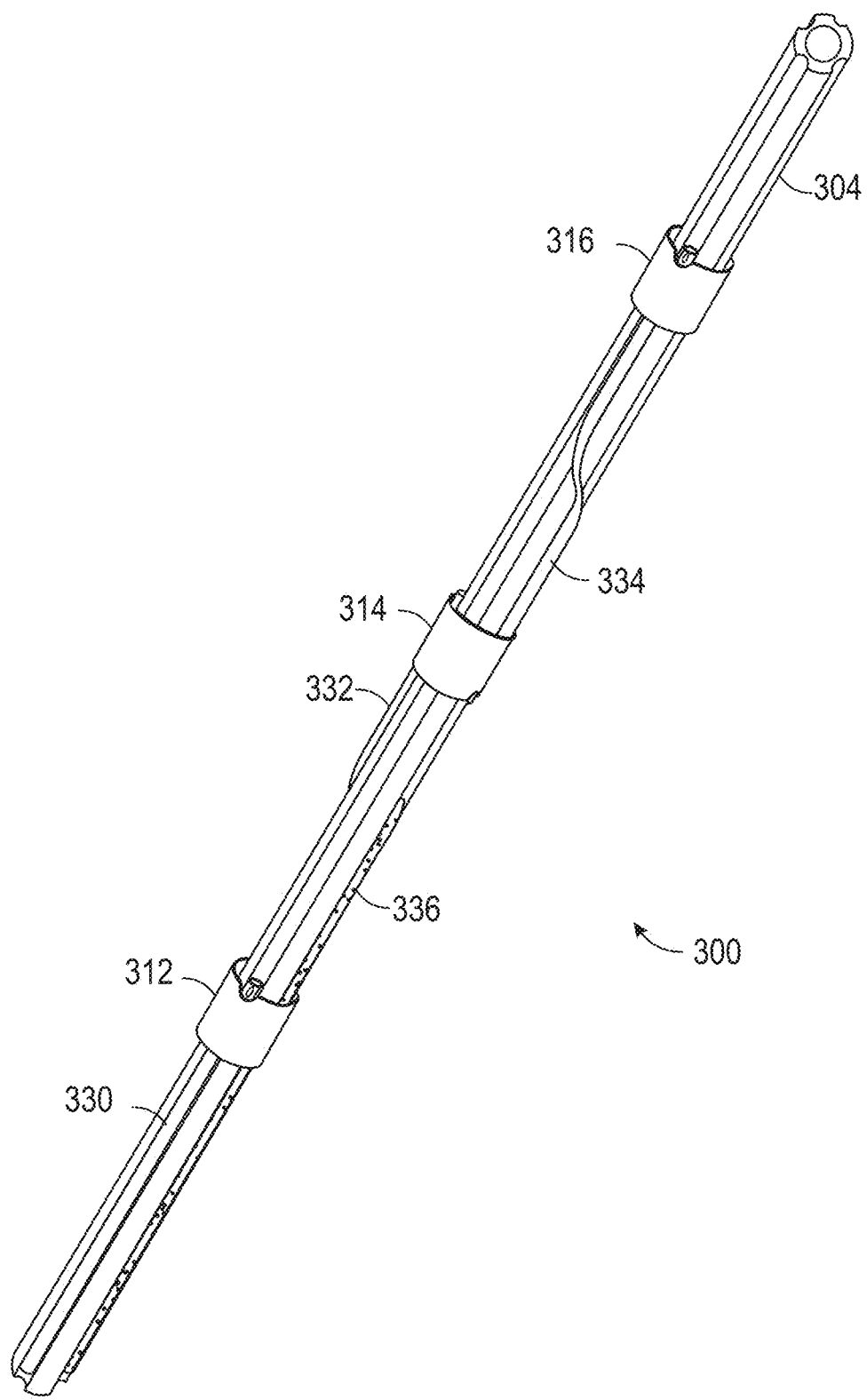
FIG. 3A depicts a set of shock wave electrode assemblies in an exemplary shock wave angioplasty device that may be activated to generate shock waves at 6 locations, in accordance with some embodiments.
Figure 3B:
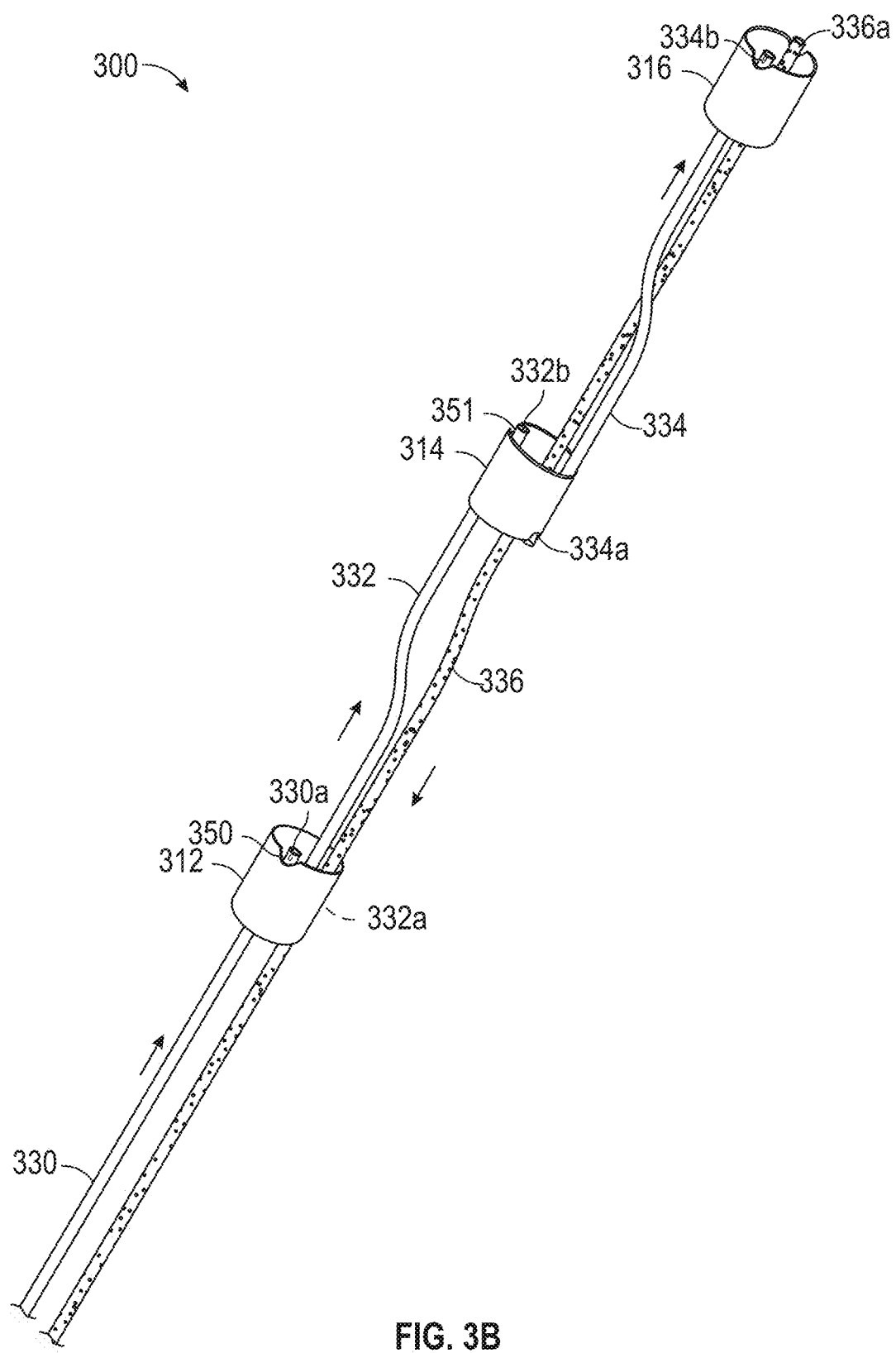
FIG. 3B depicts the connectivity between a plurality of inner electrodes and sheaths to attain the configuration of FIG. 3A, in accordance with some embodiments.

FIGS. 3A-3B depict another set of shock wave electrode assemblies that may be included in an exemplary shock wave angioplasty device such as the device depicted in FIG. 1. As discussed above, FIGS. 2A-2E relate to an exemplary configuration of electrode assemblies that may be activated to generate shock waves at 4 locations. In contrast, FIGS. 3A-3B relate to an exemplary configuration of electrode assemblies that may be activated to generate shock waves at 6 locations, as discussed below.

As depicted in FIG. 3A, an exemplary shock wave angioplasty device 300 comprises an elongated tube 304 having four longitudinal grooves on the outer surface. A first conductive sheath 312, a second conductive sheath 314, and a third conductive sheath 316 are each circumferentially mounted around the elongated tube 304. A number of insulated wires 330, 332, 334, and 336 are disposed on the outer surface of the elongated tube 304 such that they extend along the outer surface of the elongated tube. In particular, the insulated wire 330 is disposed within a single groove in its entirety, while the insulated wires 332, 334, and 336 are each disposed within multiple grooves. For example, as shown in FIG. 3A, the insulated wire 334 includes a first straight portion disposed within one groove, a second straight portion disposed within the adjacent groove, and a curved portion disclosed between the two grooves.

The conductive sheaths 312, 314, and 316 and the insulated wires 330, 332, 334, and 336 form three electrode assemblies that can be activated to generate shock waves at 6 locations. Turning to FIG. 3B, a portion of the insulated wire 330 is removed to form a first inner electrode 330a. As discussed above, a portion of the insulating layer of the wire 330 may be removed by cutting a hole in the insulating layer near the distal end of the wire 330 to expose an electrically conductive wire portion along the length of the wire, forming the first inner electrode 330a. Alternatively, the inner electrode 330a may be formed by cutting the distal end of the wire to expose an electrically conductive cross-section of the wire. As shown, the first inner electrode 330a is adjacent to, but not in contact with, the distal side edge of the first conductive sheath 312. In operation, the first conductive sheath 312 acts as an outer electrode and a first shock wave is created across the first inner electrode 330a and the distal side edge of the first conductive sheath 312.

Furthermore, a second inner electrode 332a and a third inner electrode 332b are formed by removing a portion of the insulated wire 332 (e.g., cutting a hole in the insulating layer, cutting the end of the wire to expose an electrically conductive cross section) near the proximal end and removing a portion of the insulated wire 332 near the distal end, respectively. A fourth inner electrode 334a and a fifth inner electrode 334b are formed by removing a portion of the insulated wire 334 near the proximal end and removing a portion of the insulated wire 334 near the distal end, respectively. A sixth inner electrode 336a is formed by removing a portion of the insulated wire 336 near the distal end.

In operation, the proximal end of the insulated wire 330 and the proximal end of the insulated wire 336 are connected to the output ports of a high voltage pulse generator (e.g., the high voltage pulse generator 150 in FIG. 1). A high voltage is applied across the insulated wire 330 and 336 such that a current flows as indicated by the arrows in FIG. 3B, with the insulated wire 336 as the common ground wire. Specifically, the current traverses from the insulated wire 330 to the distal side edge of the first conductive sheath 312, creating a first shock wave across the first inner electrode 330a and the distal side edge. The current then traverses from the proximal side edge of the first conductive sheath 312 to the insulated wire 332, creating a second shock wave across the proximal side edge and the second inner electrode 332a. The first inner electrode 330a and the second inner electrode 332a are positioned circumferentially 180 degrees from each other. As such, the first shock wave and the second shock wave may propagate in opposite directions, extending outward from the side of the elongated tube.

The current then traverses from insulated wire 332 to the distal side edge of the second conductive sheath 314, creating a third shock wave across the third inner electrode 332b and the distal side edge. The current then traverses from the proximal side edge of the second conductive sheath 314 to the insulated wire 334, creating a fourth shock wave across the proximal side edge of the second conductive sheath 314 and the fourth inner electrode 334a. The third inner electrode 332b and the fourth inner electrode 334a are positioned circumferentially 180 degrees from each other. Further, the first inner electrode 330a and the third inner electrode 332b are positioned circumferentially 90 degrees from each other. As depicted in FIG. 3B, the first inner electrode 330a is positioned adjacent to an arcuate cut-out 350 on the distal side edge of the first conductive sheath 312, while the third inner electrode 332b is positioned adjacent to an arcuate cut-out 351 on the distal side edge of the second conductive sheath. As depicted, the two cut-outs 350 and 351 are positioned circumferentially 90 degrees from each other.

The current then traverses from the insulated wire 334 to the distal side edge of the third conductive sheath 316, creating a fifth shock wave across the distal side edge of the third conductive sheath 316 and the fifth inner electrode 334b. The current then traverses from the distal side edge of the third conductive sheath 316 to the insulated wire 336, creating a sixth shock wave across the distal side edge of the third conductive sheath 316 and the sixth inner electrode 336a. The current then returns to the output port (not depicted), which may be a negative channel or a ground channel.

In the depicted example in FIG. 3B, the first shock wave and the second shock wave are generated on the distal side edge and the proximal side edge of the first conductive sheath 312, respectively, due to the diagonal placement of the inner electrodes 330a and 332a relative to the first conductive sheath 312. The diagonal placement of the inner electrodes allows the sonic output to be distributed more evenly longitudinally along the balloon while making the shock waves less annular. In contrast, the fifth shock wave and the sixth shock wave are both generated on the distal side edge of the third conductive sheath 316, due to the placement of the inner electrodes 334b and 336a relative to the third conductive sheath 316. These configurations maintain the continuity in case a wire breaks at the firing spot. One of ordinary skill in the art should recognize that the location of a shock wave can be configured in a flexible manner by arranging the corresponding wire and the corresponding conductive sheath (and the location of the corresponding cut-out on the sheath, if available) accordingly.

FIGS. 4A-D depict another set of shock wave electrode assemblies that may be included an exemplary shock wave angioplasty device such as the device depicted in FIG. 1. As described above, the embodiments depicted in FIGS. 2A-2E and FIGS. 3A-B can each generate shock waves at multiple locations (4 and 6 respectively) via a single current. In contrast, the embodiment depicted in FIGS. 4A-D relate to an exemplary configuration of electrode assemblies that may be activated to generate multiple shock waves via multiple currents, as discussed below. Specifically, two separate currents are generated in order to create shock waves in eight locations.

Figure 4A:
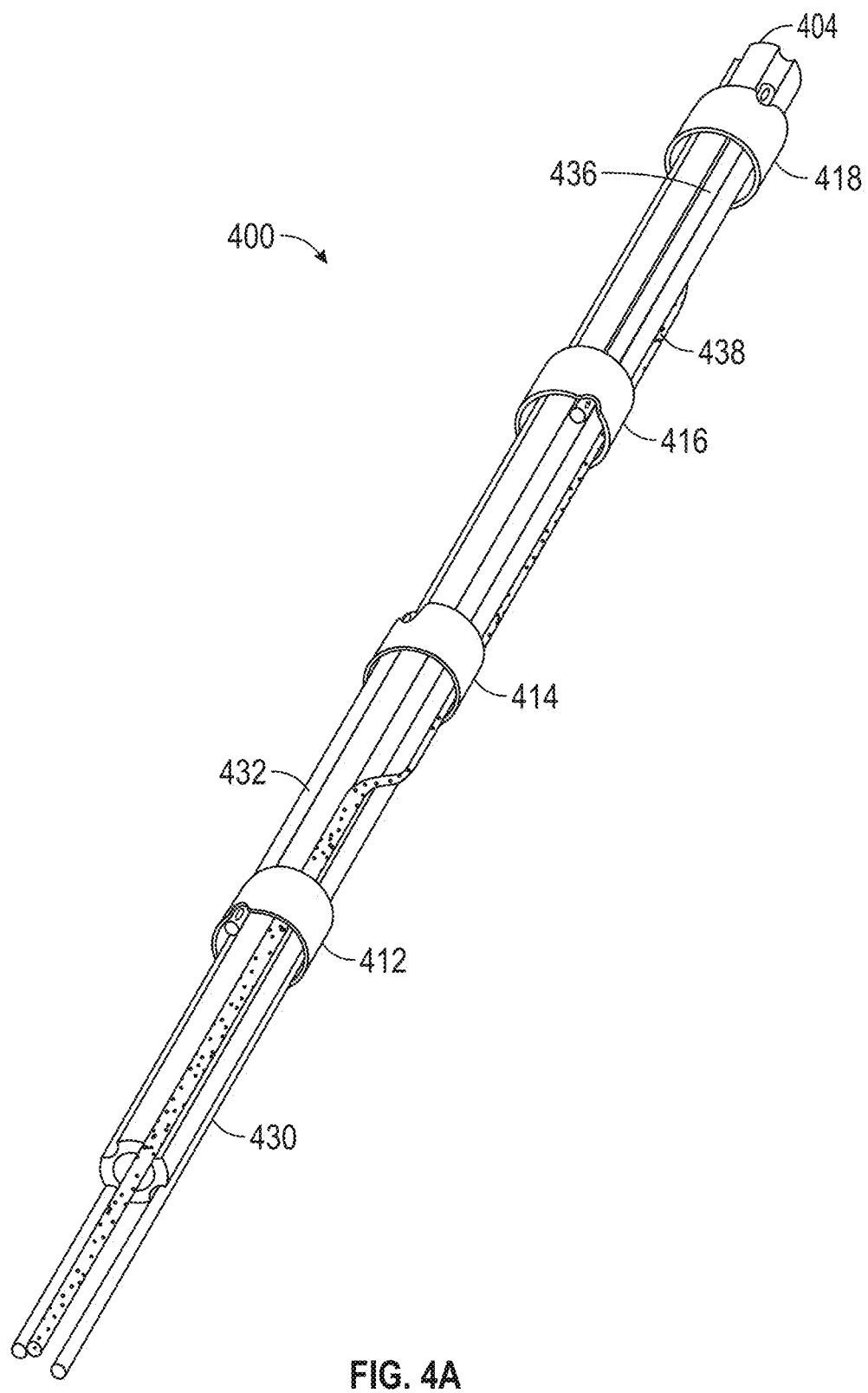
FIG. 4A depicts a set of shock wave electrode assemblies in an exemplary shock wave angioplasty device that may be activated to generate shock waves at 8 locations, in accordance with some embodiments.
Figure 4B:
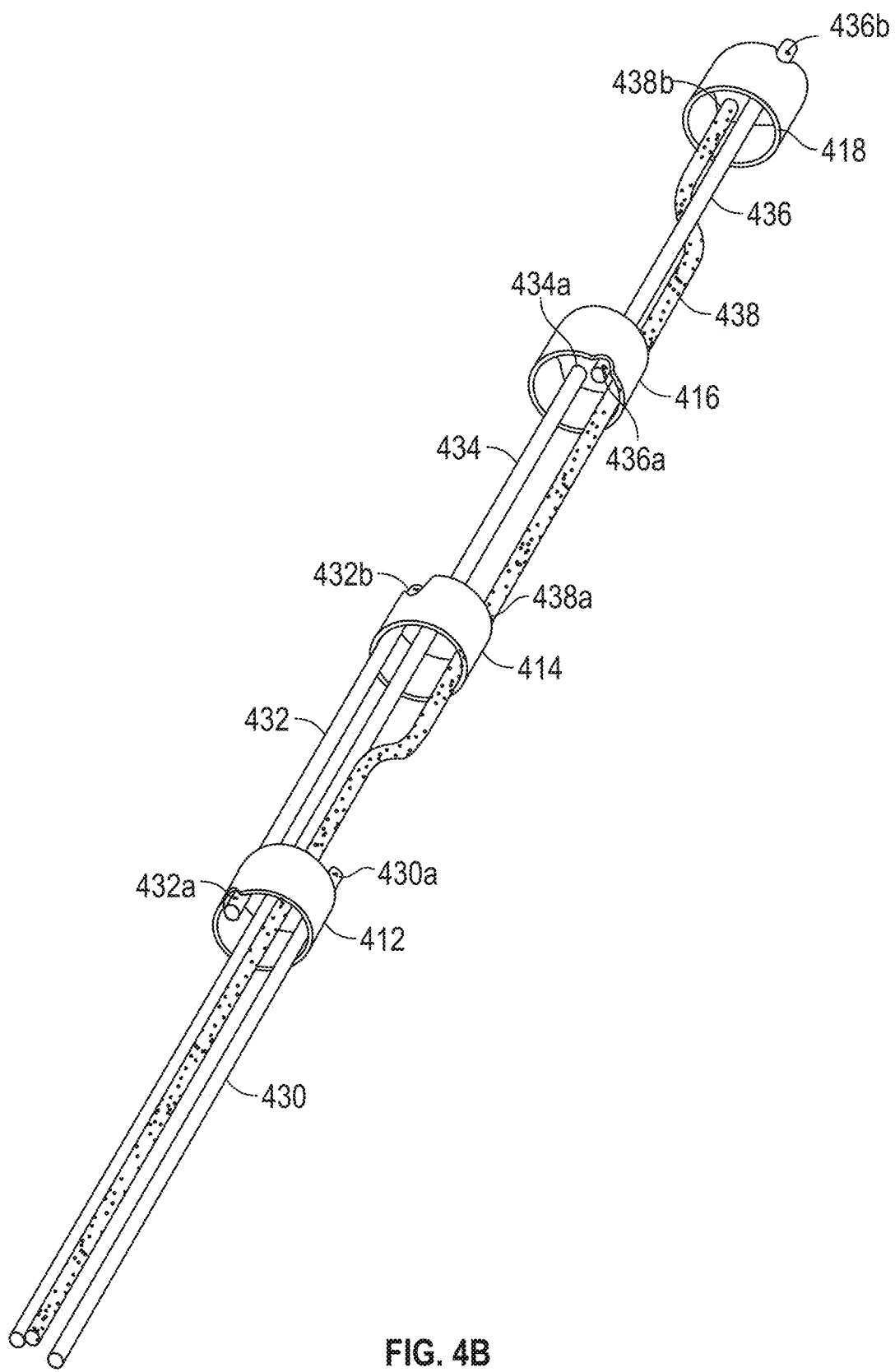
FIG. 4B depicts the connectivity between a plurality of inner electrodes and sheaths to attain the configuration of FIG. 4A, in accordance with some embodiments.

As depicted in FIG. 4A and FIG. 4B, an exemplary shock wave angioplasty device 400 comprises an elongated tube 404 having four longitudinal grooves on the outer surface. A first conductive sheath 412, a second conductive sheath 414, a third conductive sheath 416, and a fourth conductive sheath 418 are each circumferentially mounted around the elongated tube 404. A number of insulated wires 430, 432, 434, 436, and 438 are disposed on the outer surface of the elongated tube 404 such that they extend along the outer surface of the elongated tube. In particular, some insulated wires (e.g., insulated wires 432 and 436) are each disposed within a single groove in its entirety, while some insulated wires (e.g., insulated wires 434 and 438) are each disposed within multiple grooves.

The conductive sheaths 412, 414, 416, and 418 and the insulated wires 430, 432, 434, 436, and 438 form four electrode assemblies that can be activated to generate shock waves at 8 locations. Turning to FIG. 4B, a portion of the insulated wire 430 is removed to form a first inner electrode 430*a*. Furthermore, a second inner electrode 432*a* and a third inner electrode 432*b* are formed by removing a portion of the insulated wire 432 near the proximal end and removing a portion of the insulated wire 432 near the distal end, respectively. A fourth inner electrode 438*a* is formed by removing a portion of the insulated wire 438. A fifth inner electrode 434*a* is formed by removing a portion of the insulated wire 434 near the distal end. A sixth inner electrode 436*a* and a seventh inner electrode 436*b* are formed by removing a portion of the insulated wire 436 near the proximal end and removing a portion of the insulated wire 436 near the distal end, respectively. An eighth inner electrode 438*b* is formed by removing a portion of the insulated wire 438 near the distal end.

Any of inner electrodes 430*a*, 432*a*, 432*b*, 434*a*, 434*b*, 436*a*, 436*b*, and 438*b* may be formed by removing a portion of the corresponding wire in any manner that can expose an electrically conductive portion of the wire, for example, by cutting a hole in the insulating layer or cutting the end of the wire to expose an electrically conductive cross section. Inner electrode 438*a* may be formed by removing a portion of the insulated wire 438 (e.g., cutting a hole in the insulating layer) on the outer surface of the wire adjacent to a side edge of the second conductive sheath 414.

FIG. 4C schematically depicts an electrical diagram of the configuration of FIGS. 4A and 4B, in accordance with some embodiments. In operation, the proximal end of the insulated wire 430 and the proximal end of the insulated wire 438 are first connected to the output ports of a high voltage pulse generator (e.g., the high voltage pulse generator 150 in FIG. 1), with the insulated wire 438 as the common ground wire. A high voltage is applied across the insulated wire 430 and 438 such that a first current 4*a* flows as indicated by the arrows in FIG. 4C. Specifically, the first current 4*a* traverses from the insulated wire 430 to the distal side edge of the first conductive sheath 412, creating a first shock wave across the first inner electrode 430*a* and the distal side edge of the first conductive sheath 412. The first current 4*a* then traverses from the proximal side edge of the first conductive sheath 412 to the insulated wire 432, creating a second shock wave across the proximal side edge of the first conductive sheath 412 and the second inner electrode 432*a*. The current then traverses from insulated wire 432 to the distal side edge of the second conductive sheath 414, creating a third shock wave across the third inner electrode 432*b* and the distal side edge of the second conductive sheath 414. The current then traverses from the proximal side edge of the second conductive sheath 414 to the insulated wire 438, creating a fourth shock wave across the proximal side edge of the second conductive sheath 414 and the fourth inner electrode 438*a*. The current then returns to the output port (not depicted), which may be a negative channel or a ground channel.

FIG. 4D schematically depicts another electrical diagram of the configuration of FIGS. 4A and 4B, in accordance with some embodiments. The proximal end of the insulated wire 434 and the proximal end of the insulated wire 438 can be connected to the output ports of the high voltage pulse generator (e.g., the high voltage pulse generator 150 in FIG. 1). The high voltage is applied across the insulated wire 434 and 438 such that a second current 4*b* flows as indicated by the arrows in FIG. 4C. Specifically, the first current 4*b* traverses from the insulated wire 434 to the distal side edge of the third conductive sheath 416, creating a fifth shock wave across the fifth inner electrode 434*a* and the distal side edge of the third conductive sheath 416. The second current 4*b* then traverses from the proximal side edge of the third conductive sheath 416 to the insulated wire 436, creating a sixth shock wave across the proximal side edge of the third conductive sheath 416 and the sixth inner electrode 436*a*. The current then traverses from insulated wire 436 to the distal side edge of the fourth conductive sheath 418, creating a seventh shock wave across the seventh inner electrode 436*b* and the distal side edge of the fourth conductive sheath 418. The current then traverses from the distal side edge of the fourth conductive sheath 418 to the insulated wire 438, creating a eighth shock wave across the distal side edge of the fourth conductive sheath 418 and the eighth inner electrode 438*b*. The current then returns to the output port (not depicted), which may be a negative channel or a ground channel.

As such, in the embodiment shown in FIGS. 4A-D, two voltage channels are used to generate two separate current flows, which in turn generate shock waves at 8 different locations. In some embodiments, the high voltage pulse generator may drive the insulated wire 430 and 434 simultaneously. For example, the physician may simultaneously connect the insulated wire 430 to a first positive lead of the pulse generator, connect the insulated wire 434 to a second positive lead of the pulse generator, and connect the insulated wire 438 to a negative lead or the ground. In some embodiments, the high voltage pulse generator may apply voltage pulses sequentially (e.g., a voltage pulse is applied to the insulated wire 430 without applying a pulse to the insulated wire 434). In some embodiments, the voltage pulses applied to the insulated wire 434 may be delayed with respect to the voltage pulses applied to the insulated wire 430. In some embodiments, a multiplexor may be used with the high voltage pulse generator to control application of pulses. This may allow shock waves with different frequency, magnitude, and timing to be generated along the elongated tube. In the depicted embodiment in FIGS. 4A-D, the two voltage channels share the same common ground wire (i.e., insulated wire 438). One of ordinary skill in the art should understand that any number of voltage channels (e.g., 4) may be configured around a single elongated tube, and these voltage channels may rely on the same or different common ground wires.

In contrast with the embodiment depicted in FIGS. 3A-B, in which three electrode assemblies are connected in series, the embodiment depicted in FIGS. 4A-D is configured such that some of the electrode assemblies (e.g., any electrode assembly on the path of current 4a vs. any electrode assembly on the path of current 4b) operate on different voltage channels. The series configuration (e.g., as shown in FIGS. 3A-B) may allow for more shock waves to be simultaneously generated using fewer wires than if, for example, each electrode assembly is connected to a separate voltage channel. Reducing the number of wires along the length of the elongated tube may help to maintain the ability of the elongated tube to bend and flex (e.g., to navigate through tortuous vasculature) and fit into more treatment areas. On the other hand, the voltage applied to a series configuration needs to be greater and/or of longer duration than the voltage applied to electrode assemblies each connected to separate voltage channels in order to attain a shock wave of similar magnitude. As such, a shock wave as depicted in FIG. 4A-D, in which some electrode assemblies are connected in series (e.g., conductive sheaths 412 and 414) while some electrode assemblies are controlled by different voltage channels (e.g., conductive sheaths 412 and 416), may provide the ability to apply a stronger shock wave when desired, but also have the ability to simultaneously apply many shock waves without substantially compromising the flexibility and turning capability of the device by minimizing the number of wires.

Figure 5:
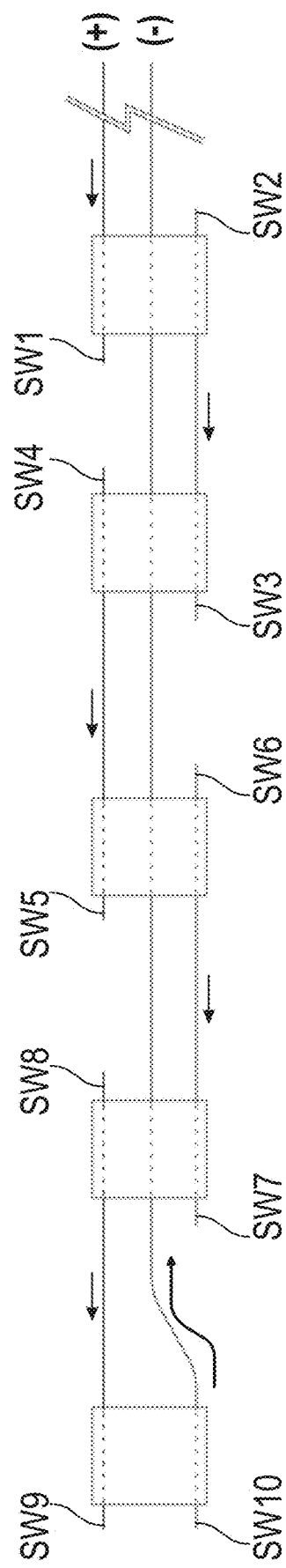
FIG. 5 depicts a set of shock wave electrode assemblies in an exemplary shock wave angioplasty device that may be activated to generate shock waves at 10 locations, in accordance with some embodiments.

It should be appreciated that a shock wave device may include any number of conductive sheaths and thus, any number of electrode assemblies. FIG. 5 depicts another set of shock wave electrode assemblies that may be included an exemplary shock wave angioplasty device such as the device depicted in FIG. 1. The embodiment depicted in FIG. 5 relates to an exemplary configuration of electrode assemblies that may be activated to generate 10 shock waves via a single voltage channel. As depicted in FIG. 5, the shock wave device includes five conductive sheaths and six wires. In operation, in response to a voltage being applied, a current flows through the six wires as indicated by the arrows, generating ten shockwaves (SW1-SW10) as illustrated.

Figure 6A:
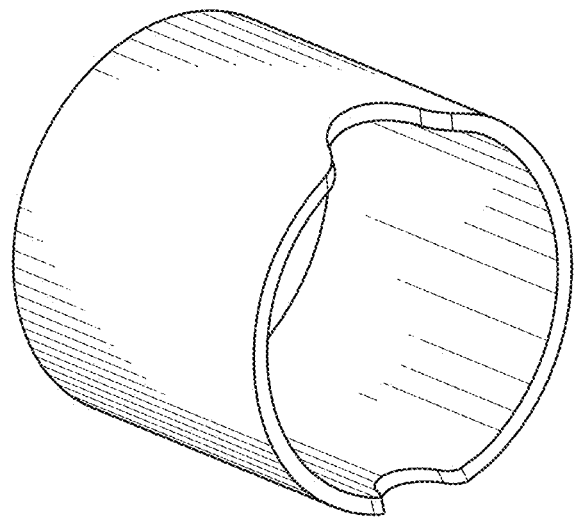
FIG. 6A depicts an exemplary sheath that may be used in an electrode assembly, in accordance with some embodiments.
Figure 6B:
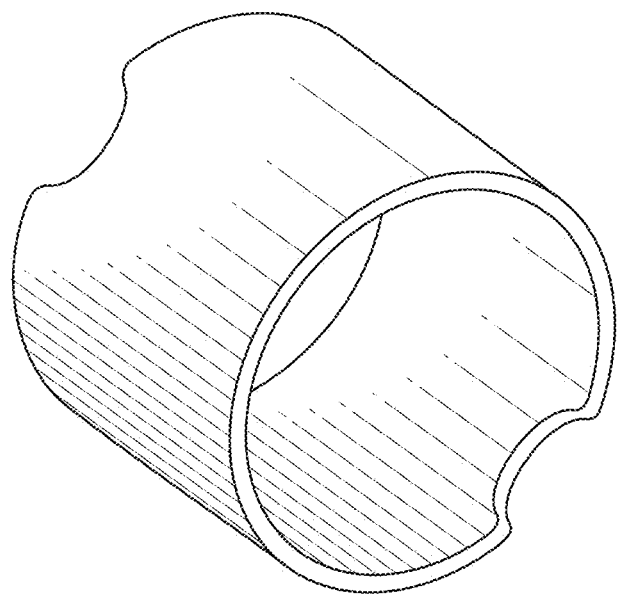
FIG. 6B depicts an exemplary sheath that may be used in an electrode assembly, in accordance with some embodiments.

With reference to FIGS. 1-5, each of the above-described conductive sheaths may be constructed in any electrically conductive material and may take any shape. As discussed above, any number of cut-outs may be created on a conductive sheath to improve the performance of the electrode assembly. In some embodiments, the number and locations of the cut-outs on the conductive sheath may vary based on the intended configuration of the electrode assembly. For example, a conductive sheath depicted in FIG. 6A includes two cut-outs positioned circumferentially 180 degrees from each other on the same side edge. This embodiment can be used to construct an electrode assembly that generates two shock waves that are circumferentially 180 degrees from each other on the same side edge of the conductive sheath, such as the conductive sheaths 214, 316, and 418. As another example, a conductive sheath depicted in FIG. 6B includes two cut-outs positioned circumferentially 180 degrees from each other on opposite side edges of the conductive sheath. This embodiment can be used to construct an electrode assembly that generates two shock waves that are circumferentially 180 degrees from each other on the opposite side edges of the conductive sheath, such as the conductive sheaths 212, 312, and 412. In some embodiments, a sheath having a larger number of cut-outs may be created to improve the versatility of the sheath and reduce manufacture cost. For example, a sheath having four cut-outs that are positioned circumferentially 90 degrees apart on each side edge of the conductive sheath can be used in place of any of the above-described conductive sheaths.

Figure 6C:
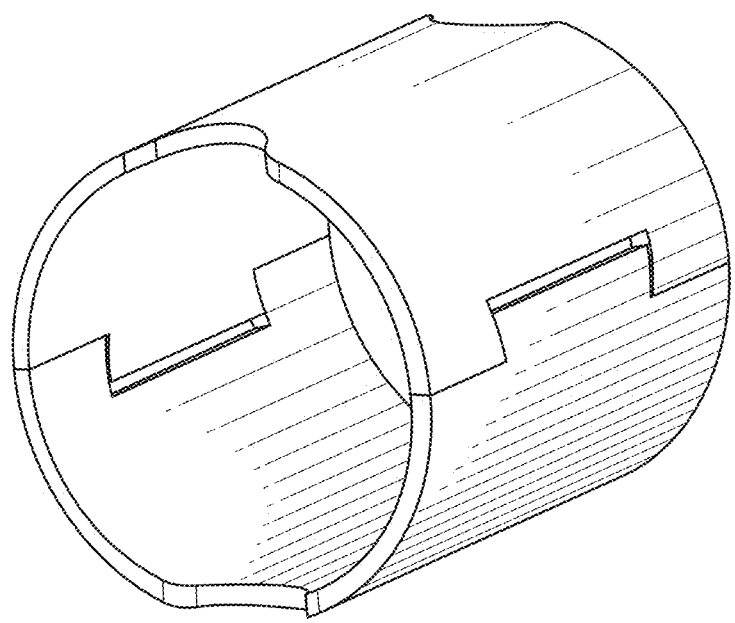
FIG. 6C depicts an exemplary sheath that may be used in an electrode assembly, in accordance with some embodiments.
Figure 6D:
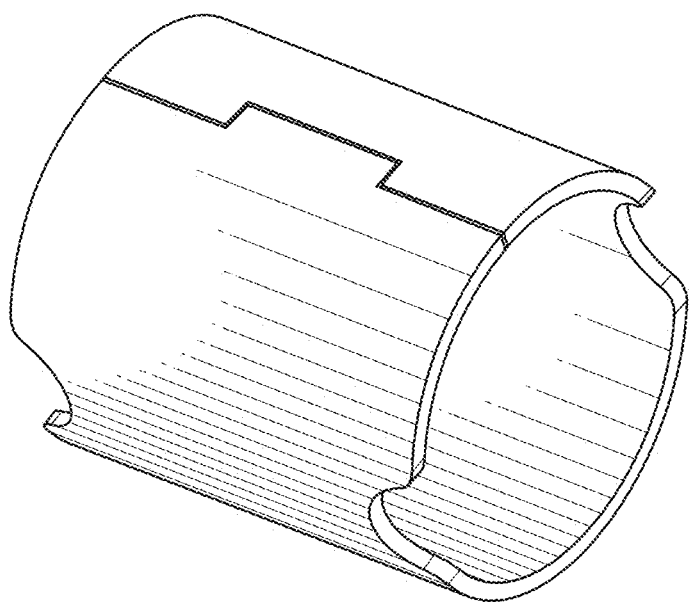
FIG. 6D depicts an exemplary sheath that may be used in an electrode assembly, in accordance with some embodiments.

Further, a conductive sheath may be created from multiple sub-components. In some embodiments, the conductive sheath includes multiple sub-components having notches and/or recesses that may be interlocked to form the conductive sheath, such as the conductive sheath having two halves dovetailed together as depicted in FIGS. 6C-D. In some embodiments, the conductive sheath includes multiple sub-components that can be pieced together by way of any suitable method, such as soldering, crimping, welding, conductive adhesives, pressure fit, interference fit, to form the conductive sheath. The multiple sub-components may allow for easy configuration of the electrode assembly because, for example, a technician may first position the insulated wires into the grooves of the elongated tube and then crimp the two halves of the conductive sheath over the elongated tube to amount the conductive sheath.

In some embodiments, the conductive sheath is created as a single piece to minimize potential damages (e.g., scratching) to the insulated wires during assembly. In some embodiments, during assembly, the elongated tube is stretched to reduce its circumference to allow a conductive sheath to be slid onto the elongated tube. The insulated wires are then positioned under the conductive sheath by, for example, sliding the wires into the grooves of the elongated tube. The elongated tube is then relaxed such that its circumference is increased and the conductive sheath is securely mounted over the elongated tube.

Figure 7A:
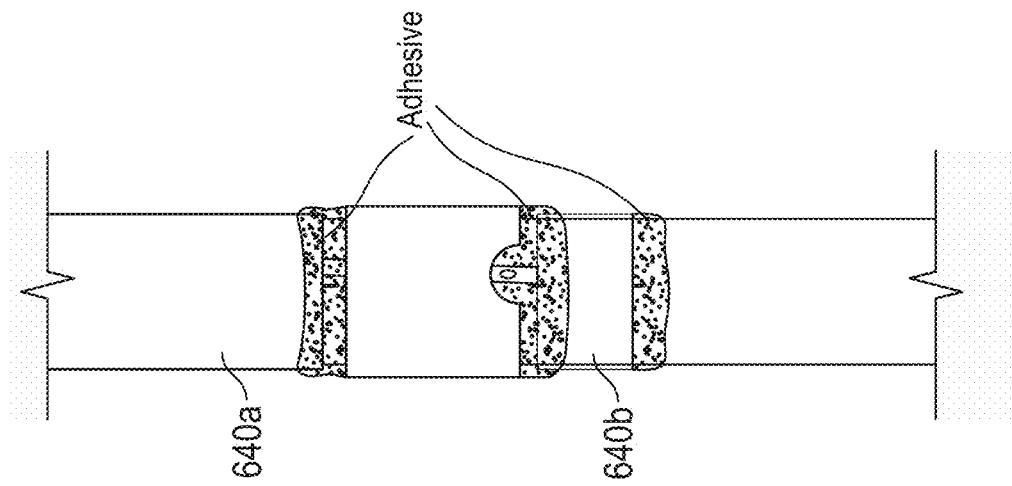
FIG. 7A depicts an exemplary construction of an electrode assembly, in accordance with some embodiments.
Figure 7B:
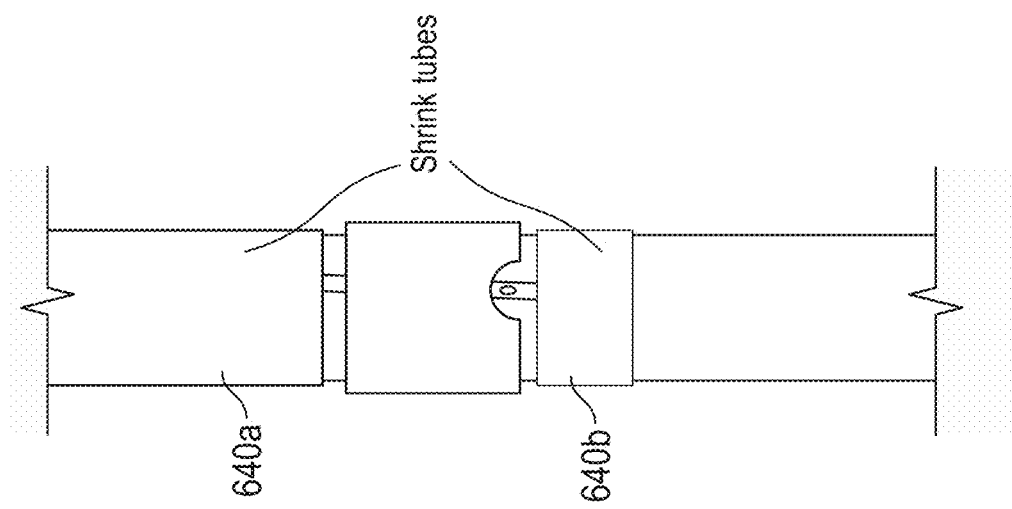
FIG. 7B depicts an exemplary construction of an electrode assembly, in accordance with some embodiments.
Figure 7C:
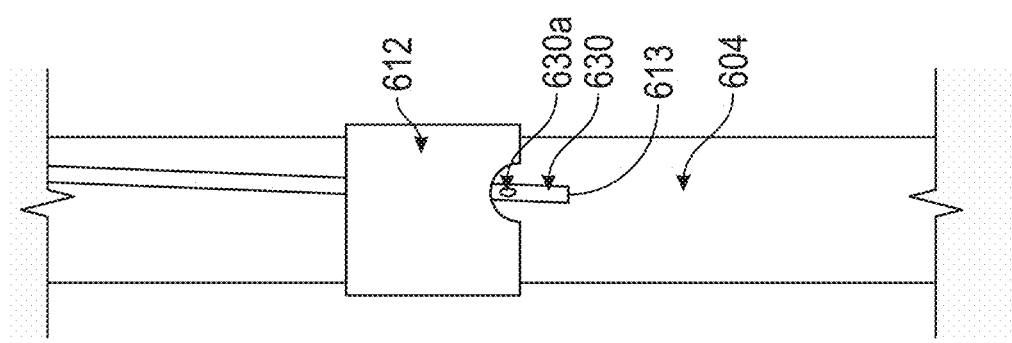
FIG. 7C depicts an exemplary construction of an electrode assembly, in accordance with some embodiments.

FIGS. 7A-C depict an exemplary construction of an electrode assembly, in accordance with some embodiments. As depicted in FIG. 7A, an insulated wire 630 is positioned on the outer surface of an elongated tube 604, and a conductive sheath 612 is circumferentially mounted on the elongated tube 604 and covers a longitudinal portion of the insulated wire. Further, a portion of the insulating layer of the wire 630 (along with any adhesives applied) is removed from the insulated wire 630 to form an inner electrode 630a. The inner electrode 630a (e.g., the inside of the wire) may be made of materials that can withstand high voltage levels and intense mechanical forces that are generated during use, for example, stainless steel, tungsten, nickel, iron, steel, and the like.

In some embodiments, one or more pieces of tubing (e.g., heat shrink tubing) may be provided over the elongated tube 604 to help retain the wire 630 within the groove while still allowing the wires to slide and move within the groove(s) to accommodate bending of the elongated tube. For example, one or more bands of shrink tubing may wrap circumferentially around one or more portions of the insulated wire 630, including one end 613 of the wire 630. In the depicted example in FIG. 7B, two bands of heat shrink tubing 640a and 640b are used to secure the wire 630, with the bottom band 640b covering the end 613 of the wire 630 and a portion of the elongated tube 604. In some embodiments, the bottom band 640b may abut up to the bottom side edge of the conductive sheath 612 while not covering insulation removal spot 630a.

The generation of plasma arcs may cause the cut-out of the sheath 612 to erode and take on a slot-like shape over time. If the end of the wire 631 is cut to form an inner electrode and the end of the wire is not secured to the elongated tube, the wire may curl up (e.g., like a candle wick) over time, compromising the effectiveness and longevity of the electrode assembly. By forming the inner electrode using an insulation removal spot 630a and securing the end of the wire to the elongated tube using a shrink tube, the life of the electrode assembly is extended.

Alternatively or additionally, adhesives (e.g., dots of conductive epoxy) may be applied along a portion of the wire and/or near the conductive sheath to partially secure or retain the wire within the groove(s) while still maintaining the ability of the wire to partially move and shift as the elongated tube bends or curves. In the depicted example in FIG. 7C, adhesives are applied along the side edges of the conductive sheath 612 and the side edges of the tubing.

In each of the embodiments depicted in FIGS. 2A, 3A, and 4A, the elongated tube includes four longitudinal grooves, spaced circumferentially 90 degrees apart, for accommodating insulated wires. It should be appreciated that the elongated tube can include any number of grooves (e.g., 6, 8). For example, for a relatively long balloon housing a large number of conductive sheaths along the length of the balloon, a larger number of wires may be required. Such system would be easier to construct, configure, and/or operate using an elongated tube having a larger number of grooves.

Any of the shock wave assemblies described herein may be used in an angioplasty procedure for breaking up calcified plaques accumulated along the walls of a vessel. One variation of a method may comprise advancing a guide wire from an entry site on a patient (e.g., an artery in the groin area of the leg) to the target region of a vessel (e.g., a region having calcified plaques that need to be broken up). A shock wave device comprising an elongated tube with a guide wire lumen, one or more electrode assemblies located along the elongated tube, and a balloon may be advanced over the guide wire to the target region of the vessel. The shock wave electrode assemblies may be any of the electrode assemblies described herein. The balloon may be collapsed over the elongated member while the device is advanced through the vasculature. The location of the shock wave device may be determined by x-ray imaging and/or fluoroscopy. When the shock wave device reaches the target region, the balloon may be inflated by a conductive fluid (e.g., saline and/or saline mixed with an image contrast agent). The one or more electrode assemblies may then be activated to generate shock waves to break up the calcified plaques. The progress of the plaque break-up may be monitored by x-ray and/or fluoroscopy. The shock wave device may be moved along the length of the vessel if the calcified region is longer than the length of the catheter with the electrode assemblies, and/or if the calcified region is too far away from the electrode assemblies to receive the full force of the generated shock waves. For example, the shock wave device may be stepped along the length of a calcified vessel region to sequentially break up the plaque. The electrode assemblies of the shock wave device may be connected in series and/or may be connected such that some electrode assemblies are connected to separate high voltage channels, which may be activated simultaneously and/or sequentially, as described above. Once the calcified region has been sufficiently treated, the balloon may be inflated further or deflated, and the shock wave device and guide wire may be withdrawn from the patient.

It will be understood that the foregoing is only illustrative of the principles of the invention, and that various modifications, alterations and combinations can be made by those skilled in the art without departing from the scope and spirit of the invention. Any of the variations of the various shock wave devices disclosed herein can include features described by any other shock wave devices or combination of shock wave devices herein. Furthermore, any of the methods can be used with any of the shock wave devices disclosed. Accordingly, it is not intended that the invention be limited, except as by the appended claims. For all of the variations described above, the steps of the methods need not be performed sequentially

What is claimed is:

1. A device for generating shock waves, the device comprising:
   an elongated tube;
   a conductive sheath circumferentially mounted around the elongated tube;
   a flexible member surrounding the sheath, the flexible member being fillable with a conductive fluid;
   a first insulated wire extending along the outer surface of the elongated tube, wherein a portion of the first insulated wire is removed to form a first inner electrode and wherein the first inner electrode is adjacent to a first end of the conductive sheath;
   a second insulated wire extending along the outer surface of the elongated tube, wherein a portion of the second insulated wire is removed to form a second inner electrode and wherein the second inner electrode is adjacent to a second end of the conductive sheath;
   wherein, when a high voltage is applied across the first inner electrode and the second inner electrode, a current is configured to flow from the first wire to the first end of the conductive sheath and from the second end of the conductive sheath to the second wire,
   wherein a first shock wave is created across the first end of the conductive sheath and the first inner electrode, and
   wherein a second shock wave is created across the second end of the conductive sheath and the second inner electrode.

2. The device of claim 1, wherein the first end and the second end are the same end of the sheath.

3. The device of claim 1, wherein the first end and the second end are different ends of the sheath.

4. The device of claim 1, wherein the elongated tube includes a first groove and a second groove along the length of the elongated tube, and wherein at least a portion of the first wire is disposed within the first groove and at least a portion of the second wire is disposed within the second groove.

5. The device of claim 1, further comprising a first piece of tubing wrapping around another portion of the first wire to secure the first wire to the elongated tube, and a second piece of tubing wrapping around another portion of the second wire to secure the second wire to the elongated tube.

6. The device of claim 1, wherein the first insulated wire comprises an insulating layer wrapping around the length of the first insulated wire, and wherein the distal end of the first wire is exposed from the insulating layer to form the first inner electrode.

7. The device of claim 1, wherein the first insulated wire comprises an insulating layer wrapping around the first insulated wire, and wherein a strip of the insulating layer is removed to form the first inner electrode.

8. The device of claim 1, wherein the first end and the second end of the sheath are straight edges.

9. The device of claim 1, wherein the first end of the conductive sheath comprises a first arcuate cut-out, wherein the second end of the conductive sheath comprises a second arcuate cut-out, wherein the first shock wave is created across the first arcuate cut-out on the first end of the conductive sheath and the first inner electrode, and wherein the second shock wave is created across the second arcuate cut-out on the second end of the conductive sheath and the second inner electrode.

10. The device of claim 9, wherein the first arcuate cut-out is positioned circumferentially 180 degrees from the second arcuate cut-out.

11. The device of claim 1, wherein the first shock wave and the second shock wave are initiated in response to a voltage being applied to a proximal end of the first wire and a proximal end of the second wire.

12. The device of claim 1, wherein the conductive sheath is a first conductive sheath, and the device further comprising:
  a second conductive sheath circumferentially mounted around the elongated tube;
  an insulated common ground wire extending along the outer surface of the elongated tube, wherein another portion of the second insulated wire is removed to form a third inner electrode adjacent to a first end of the second sheath, wherein a portion of the insulated common ground wire is removed to form a fourth inner electrode adjacent to a second end of the second sheath;
  wherein, when a high voltage is applied across the first insulated wire and the insulated common ground wire, a current is configured to flow from the first wire to the first end of the first conductive sheath, from the second end of the first conductive sheath to the second wire, from the second wire to the first end of the second conductive sheath, and from the second end of the second conductive sheath to the insulated common ground wire, wherein a third shock wave is created across the first end of the second conductive sheath and the third inner electrode, and wherein a fourth shock wave is created across the second end of the second conductive sheath and the fourth inner electrode.

13. The device of claim 12, wherein the common ground wire comprises a first straight portion, a curved portion, and a second straight portion, and wherein the first straight portion and the second straight portion are placed in two different grooves of the elongated tube.

14. The device of claim 1, wherein the flexible member is a balloon.

15. A device for generating shock waves, the device comprising:
  an elongated tube;
  a first conductive sheath, a second conductive sheath, and a third conductive sheath, each circumferentially mounted around the elongated tube;
  a first insulated wire, a second insulated wire, a third insulated wire, and an insulated common ground wire, each extending along the outer surface of the elongated tube, wherein a portion of the first insulated wire is removed to form a first inner electrode,
    wherein two portions of the second insulated wire are removed to form a second inner electrode and a third inner electrode,
    wherein two portions of the third insulated wire are removed to form a fourth inner electrode and a fifth inner electrode,
    wherein a portion of the insulated common ground wire is removed to form a sixth inner electrode,
    wherein when a high voltage is applied across the first wire and the insulated common ground wire, a current is configured to flow:
  from the first wire to a first end of the first conductive sheath,
  from a second end of the first conductive sheath to the second wire,
  from the second wire to a end of the second conductive sheath,
  from a second end of the second conductive sheath to the third wire,
  from the third wire to a end of the third conductive sheath, from a second end of the third conductive sheath to the insulated common ground wire,
  wherein a first shock wave is created across the first end of the first conductive sheath and the first inner electrode,
  wherein a second shock wave is created across the second end of the first conductive sheath and the second inner electrode,
  wherein a third shock wave is created across the first end of the second conductive sheath and the third inner electrode,
  wherein a fourth shock wave is created across the second end of the second conductive sheath and the fourth inner electrode,
  wherein a fifth shock wave is created across the first end of the third conductive sheath and the fifth inner electrode,
  wherein a sixth shock wave is created across the second end of the third conductive sheath and the sixth inner electrode.

16. The device of claim 15, wherein the first end and the second end of the third conductive sheath are the same end.

17. The device of claim 15, wherein the first end and the second end of the first conductive sheath are different ends.

18. The device of claim 15, wherein the second wire comprises a first straight portion, a curved portion, and a second straight portion, and wherein the first straight portion and the second straight portion are placed in two different grooves of the elongated tube.

19. The device of claim 15,
  wherein the first shock wave is created across an arcuate cut-out on the first end of the first conductive sheath and the first inner electrode,
  wherein the third shock wave is created across an arcuate cut-out on the first end of the second conductive sheath and the third inner electrode, and
  wherein the arcuate cut-out on the first end of the first conductive sheath is positioned circumferentially 90 degrees from the arcuate cut-out on the first end of the second conductive sheath.

20. A device for generating shock waves, the device comprising:
  an elongated tube;
  a first conductive sheath, a second conductive sheath, a third conductive sheath, a fourth conductive sheath, each circumferentially mounted around the elongated tube;
  a first insulated wire, a second insulated wire, a third insulated wire, a fourth insulated wire, and an insulated common ground wire, each extending along the outer surface of the elongated tube,
    wherein a portion of the first insulated wire is removed to form a first inner electrode,
    wherein two portions of the second insulated wire are removed to form a second inner electrode and a third inner electrode,
    wherein a portion of the third insulated wire is removed to form a fifth inner electrode,
    wherein two portions of the fourth insulated wire are removed to form a sixth inner electrode and a seventh inner electrode,
    wherein two portions of the insulated common ground wire are removed to form a fourth inner electrode and an eighth inner electrode,
    wherein, when a high voltage is applied across the first wire and the insulated common ground wire, a first current is configured to flow:
  from the first wire to a first end of the first conductive sheath to generate a first shock wave across the first end of the first conductive sheath and the first inner electrode, from a second end of the first conductive sheath to the second wire to generate a second shock wave across the second end of the first conductive sheath and the second inner electrode, from the second wire to a first end of the second conductive sheath to generate a third shock wave across the first end of the second conductive sheath and the third inner electrode, from a second end of the second conductive sheath to the insulated common ground wire to generate a fourth shock wave across the second end of the second conductive sheath and the fourth inner electrode, wherein, when a high voltage is applied across the third wire and the insulated common ground wire, a second current is configured to flow:

from the third insulated wire to a first end of the third conductive sheath to generate a fifth shock wave across the first end of the third conductive sheath and the fifth inner electrode, from a second end of the third conductive sheath to the fourth insulated wire to generate a sixth shock wave across the second end of the third conductive sheath and the sixth inner electrode, from the fourth insulated wire to a first end of the fourth conductive sheath to generate a seventh shock wave across the first end of the fourth conductive sheath and the seventh inner electrode, from a second end of the fourth conductive sheath to the insulated common ground wire to generate an eighth shock wave across the second end of the fourth conductive sheath and the eighth inner electrode.

21. The device of claim 20, wherein the first end and the second end of the first conductive sheath are different ends.

22. The device of claim 20, wherein the first end and the second end of the fourth conductive sheath are the same end.

* * * * *